US011174464B2

(12) United States Patent
Yamamoto et al.

(10) Patent No.: US 11,174,464 B2
(45) Date of Patent: Nov. 16, 2021

(54) METHOD FOR PREPARING OSTEOBLASTS AND OSTEOBLAST INDUCER

(71) Applicant: KYOTO PREFECTURAL PUBLIC UNIVERSITY CORPORATION, Kyoto (JP)

(72) Inventors: Kenta Yamamoto, Kyoto (JP); Tsunao Kishida, Kyoto (JP); Toshiro Yamamoto, Kyoto (JP); Osam Mazda, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 0 days.

(21) Appl. No.: 15/304,287

(22) PCT Filed: Apr. 17, 2015

(86) PCT No.: PCT/JP2015/061893
§ 371 (c)(1),
(2) Date: Oct. 14, 2016

(87) PCT Pub. No.: WO2015/159982
PCT Pub. Date: Oct. 22, 2015

(65) Prior Publication Data
US 2017/0037374 A1    Feb. 9, 2017

(30) Foreign Application Priority Data

Apr. 18, 2014   (JP) .............................. JP2014-086757

(51) Int. Cl.
*A61K 35/32* (2015.01)
*C12N 5/077* (2010.01)
*A61K 35/35* (2015.01)
*A61K 35/36* (2015.01)

(52) U.S. Cl.
CPC ............ *C12N 5/0654* (2013.01); *A61K 35/35* (2013.01); *A61K 35/36* (2013.01); *C12N 5/0653* (2013.01); *A61K 35/32* (2013.01); *C12N 2500/30* (2013.01); *C12N 2501/01* (2013.01); *C12N 2501/065* (2013.01); *C12N 2501/36* (2013.01); *C12N 2501/39* (2013.01); *C12N 2501/72* (2013.01); *C12N 2501/727* (2013.01); *C12N 2506/1307* (2013.01)

(58) Field of Classification Search
CPC .......... C12N 5/0654; C12N 2506/1307; C12N 2501/36; C12N 2501/065; C12N 2501/39; C12N 2500/30; C12N 2501/72; C12N 2501/01; C12N 2501/727; C12N 2502/1305; A61K 35/32
See application file for complete search history.

(56) References Cited

U.S. PATENT DOCUMENTS

2014/0356336 A1   12/2014   Egusa

FOREIGN PATENT DOCUMENTS

| EP | 3 026 112 | 6/2016 |
|----|-----------|--------|
| JP | 2002-527386 | 8/2002 |
| JP | 2008-44956 | 2/2008 |
| JP | 2011-73998 | 4/2011 |
| WO | 98/25460 | 6/1998 |
| WO | 00/21523 | 4/2000 |
| WO | 00/61576 | 10/2000 |
| WO | 2013/013105 | 1/2013 |
| WO | 2013/100080 | 7/2013 |

OTHER PUBLICATIONS

Yazawa et al., J Periodontal, 2005, vol. 76, No. 2, p. 295-302.*
Lekic et al., The anatomical Record, 1996, vol. 254 p. 327-341.*
Mostafa et al., The Open Dentistry Journal, 2011, vol. 5, p. 139-145.*
Mundy et al., Science, 1999, vol. 286, 5446, p. 1946-1949.*
International Search Report dated Jul. 21, 2015 in International (PCT) Application No. PCT/JP2015/061893.
Zhou et al., "The role of simvastatin in the osteogenesis of injectable tissue-engineered bone based on human adipose-derived stromal cells and platelet-rich plasma", Biomaterials, vol. 31, Apr. 9, 2010, pp. 5325-5335.
Suzuki et al., "An In Vitro Study on the Ectopic Calcification, Human Gingival Fibroblast Culture", J. Jpn. Stomatol. Soc., vol. 41, No. 2, Apr. 1992, pp. 268-274.
Suzuki et al., "An In Vitro Study on the Characteristics of Osteoblastic Cells Derived from Human Mandibular Periosteum", J. Jpn. Stomatol. Soc., vol. 40, No. 1, Jan. 1991, pp. 89-108.
Hou et al., "Pluripotent Stem Cells Induced from Mouse Somatic Cells by Small-Molecule Compounds", Science, vol. 341, Aug. 9, 2013, pp. 651-654.
Karner et al., "Differentiation of Human Embryonic Stem Cells Into Osteogenic or Hematopoietic Lineages: A Dose-Dependent Effect of Osterix Over-Expression", Journal of Cellular Physiology, vol. 218, 2009, pp. 323-333.
Maeda et al., "Induction of Osteoblast Differentiation Indices by Statins in MC3T3-E1 Cells", Journal of Cellular Biochemistry, vol. 92, 2004, pp. 458-471.

(Continued)

*Primary Examiner* — Kade Ariani
(74) *Attorney, Agent, or Firm* — Wenderoth, Lind & Ponack, L.L.P.

(57) ABSTRACT

An object of the present invention is to provide a method for preparing osteoblasts that are applicable, without causing risk of canceration, to bone defect repair or to the treatment of bone resorption, fracture, osteoporosis, or the like. To solve this problem, the present invention provides a method for preparing osteoblasts, the method comprising culturing mammal differentiated somatic cells in a medium in the presence of at least one compound selected from the group consisting of (1) statin compounds, (2) casein kinase 1 inhibitors, (3) cAMP inducers, and (4) histone methyltransferase inhibitors, to convert the somatic cells into osteoblasts.

3 Claims, 11 Drawing Sheets

(56) References Cited

OTHER PUBLICATIONS

Maeda et al., "Simvastatin Promotes Osteoblast Differentiation and Mineralization in MC3T3-E1 Cells", Biochemical and Biophysical Research Communications, vol. 280, 2001, pp. 874-877.
Qiao et al., "Simvastatin Promotes Osteogenic Differentiation of Mouse Embryonic Stem Cells Via Canonical Wnt/β-Catenin Signaling", Mol. Cells, vol. 32, Nov. 30, 2011, pp. 437-444.
Aghaloo et al., "Oxysterols Enhance Osteoblast Differentiation In Vitro and Bone Healing In Vivo", Journal of Orthopaedic Research, vol. 25, Jun. 2007, pp. 1488-1497.
Park et al., "The Small Molecule Phenamil Induces Osteoblast Differentiation", Molecular and Cellular Biology, vol. 29, No. 14, Jul. 2009, pp. 3905-3914
Ruiz-Gaspa et al., "Simvastatin and Atorvastatin Enhance Gene Expression of Collagen Type 1 and Osteocalcin in Primary Human Osteoblasts and MG-63 Cultures", Journal of Cellular Biochemistry, vol. 101, 2007, pp. 1430-1438.
Zhao et al., "Simvastatin induces the osteogenic differentiation of human periodontal ligament stem cells", Fundamental & Clinical Pharmacology, vol. 28, 2014, pp. 583-592.
Uzzan et al., "Effects of statins on bone mineral density: A meta-analysis of clinical studies", Bone, vol. 40, 2007, pp. 1581-1587.
Minami et al., "A Small Molecule that Promotes Cardiac Differentiation of Human Pluripotent Stem Cells under Defined, Cytokine- and Xeno-free Conditions", Cell Reports, vol. 2, Nov. 29, 2012, pp. 1448-1460.
Mundy et al., "Stimulation of Bone Formation in Vitro and in Rodents by Statins", Science, 286(5446):1946-1949 (1999).
Fujioka et al., "Directly Reprogrammed Osteoblasts Genetically Engineered to produce Interleukin-10 Significantly Suppress Osteoclastgenesis", Annals of the Rheumatic Diseases, 73(Suppl.2): 794.1-794 (2014).
Mizoshiri et al., "Transduction of Oct6 or Oct9 gene concomitant with Myc family gene induced osteoblast-like phenotypic conversion in normal human fibroblasts", Biochemical and Biophysical Research Communications, 467(4):1110-1116 (2015).
Yamamoto et al., "Direct conversion of human fibroblasts into functional osteoblasts by defined factors", Proceedings National Academy of Sciences, 112(19):6152-6157 (2015).
Extended European Search Report dated Nov. 8, 2017 in European Patent Application No. 15779733.3.
Shui et al., "Mouse Embryo-Derived NIH3T3 Fibroblasts Adopt an Osteoblast-Like Phenotype When Treated With 1α,25-Dihydroxyvitamin $D_3$ and Dexamethasone In Vitro", Journal of Cellular Physiology, 2002, vol. 193, pp. 164-172.
Choe et al., "Continuously Generated $H_2O_2$ Stimulates the Proliferation and Osteoblastic Differentiation of Human Periodontal Ligament Fibroblasts", Journal of Cellular Biochemistry, 2012, vol. 113, No. 4, pp. 1426-1436.
Hee et al., "Influence of three-dimensional scaffold on the expression of osteogenic differentiation markers by human dermal fibroblasts", Biomaterials, 2006, vol. 27, pp. 875-884.
Ducy et al., "The Osteoblast: A Sophisticated Fibroblast under Central Surveillance", Science, 2000, vol. 289, pp. 1501-1504.
Yoshitatsu et al., "Differentiation Potential of The Human Dermal Fibroblasts (hDFBs)", Journal of Japan Society of Plastic and Reconstructive Surgery, 2011, vol. 31, pp. 453-461, with English Abstract.

* cited by examiner 28 days 28 days 28 days

HDFs: Human dermal fibroblasts
OBs: Osteoblasts
SS: Cells cultured with the addition of simvastatin
SS+D: cells cultured with the addition of simvastatin and D4476

FBs: Fibroblasts
OBs: Osteoblasts
SS: Cells cultured with the addition of simvastatin
SS+D: Cells cultured with the addition of simvastatin and D4476

Fibroblasts    SS + D

METHOD FOR PREPARING OSTEOBLASTS AND OSTEOBLAST INDUCER

TECHNICAL FIELD

The present invention relates to a method for preparing osteoblasts, and to an osteoblast inducer. The present invention further relates to a kit for inducing somatic cells into osteoblasts.

BACKGROUND ART

There are examples of various diseases in which bone remodeling does not sufficiently function, allowing bone destruction to progress or bone defects to remain. Such diseases include fractures associated with osteoporosis, joint destruction associated with rheumatoid arthritis, a wide range of bone defects associated with serious external injuries or bone-tumor resection, and alveolar bone absorption associated with serious periodontal diseases. There are also many examples in which elderly people, in particular, suffer from disorders or prolonged bed rest due to a delay in bone regeneration after fracture, posing a large social medical problem.

Osteoblasts are cells that play a central role in bone formation and remodeling. In osteoporosis and rheumatoid arthritis, osteoclasts are activated, reducing bone density and strength. If it is possible to achieve, an increase in the number of osteoblasts and an increase in the function thereof can serve as a useful prevention or treatment method. Further, autologous bone marrow cell transplants have been performed to treat bone defect lesions, and it is believed that osteoblasts differentiated from bone marrow mesenchymal stem cells accelerate bone regeneration. However, bone marrow harvesting is very invasive for patients, and according to many examples, an insufficient number of cells are obtained under existing circumstances. If it is possible to prepare a large number of osteoblasts of patients and perform autografting to a bone defect site, the above diseases can possibly effectively be treated.

Non-patent Literature 1 performs introduction of lentiviral vector of osterix into human ES cells, and differentiation induction into osteoblasts in an osteogenic medium; however, such an induction of osteoblasts by transgenesis may cause a risk of canceration.

There have been reports stating that osteoblast progenitor cells, such as ES cells, MC3T3-E1 cells, and marrow stromal cells, are induced by various compounds to differentiate into osteoblasts, undergo calcification, or produce bone-related proteins.

Non-patent Literature 2 and Non-patent Literature 3 disclose allowing a statin compound to act on MC3T3-E1, which is an osteoblast progenitor cell line, to induce differentiation into osteoblasts.

Non-patent Literature 4 discloses allowing simvastatin to act on mouse ES cells to induce differentiation into osteoblasts.

Non-patent Literature 5 discloses allowing oxysterol to act on mouse marrow stromal cells to induce differentiation into osteoblasts.

Non-patent Literature 6 discloses allowing phenamil to act on mouse marrow stromal cells to induce differentiation into osteoblasts and mineralization.

Non-patent Literature 7 discloses that simvastatin and atorvastatin enhance the production of collagen Type I and osteocalcin in primary human osteoblasts and the MG-63 osteosarcoma cell line.

Non-patent Literature 8 discloses that simvastatin induces the differentiation of human periodontal ligament stem cells into osteoblasts.

Non-patent Literature 9 discloses that various statin compounds increase bone density.

All of these documents disclose a technique of inducing cells, such as ES cells, marrow stromal cells, and periodontal ligament cells, that originally have the ability to differentiate into osteoblasts, or a technique of increasing the bone formation ability of cells that are already osteoblasts.

CITATION LIST

Non-Patent Literature

NPL 1: Karner E et al., J Cell Physiol. 2009
NPL 2: T. Maeda et al., Journal of Cellular Biochemistry 92: 458-471 (2004)
NPL 3: T. Maeda et al., Biochem Biophys Res Commun 280: 874-877 (2001)
NPL 4: Ling Juan Qiao et al., Mol. Cells 32, 437-444 (2011)
NPL 5: Tara L. Aghaloo et al., Journal of Orthopaedic Research 2007, 1488-1497
NPL 6: Kye Won Park et al., Mol. Cell. Biol. vol. 29, 2009, pp. 3905-3914
NPL 7: Silvia Ruiz-Gaspa et al., Journal of Cellular Biochemistry 101: 1430-1438 (2007)
NPL 8: Bing-jiao Zhao et al., Fundamental & Clinical Pharmacology (2014), 583-592
NPL 9: B. Uzzan et al., Bone 40 (2007), 1581-1587

SUMMARY OF INVENTION

Technical Problem

An object of the present invention is to provide a technique of converting differentiated somatic cells into osteoblasts without gene introduction.

Solution to Problem

There have been no reports stating that normal somatic cells, which originally have no ability to become osteoblasts, are reprogrammed to become osteoblasts using low-molecular weight compounds, such as a statin compound. It is known that statin compounds and the like induce the differentiation of cells having the ability to differentiate into osteoblasts or increase the bone formation ability of cells that are already osteoblasts; however, whether somatic cells, which originally have no ability to become osteoblasts, can be reprogrammed into osteoblasts is a different issue. Thus, the present invention cannot be expected from the above non-patent literature. More specifically, there is no guarantee that a mechanism in which cells that have the ability to differentiate into osteoblasts differentiate into osteoblasts is identical to a mechanism in which irrelevant cells are forcibly made to undergo fate conversion into osteoblasts; thus, it is uncertain whether the same compound can be used to achieve both of the above mechanisms unless experiments are carried out. In fact, for example, a compound that induces ES cells to differentiate into myocardial cells is known; however, it has not been reported that the use of this compound achieved the conversion of fibroblasts into myocardial cells (Minami I et al., Cell Rep. 2012 Nov. 29; 2(5): 1448-60).

The present invention encompasses the following osteoblast preparation method, osteoblast inducer, and kit.

Item 1. A method for preparing osteoblasts, the method comprising culturing mammal differentiated somatic cells in a medium in the presence of at least one compound selected from the group consisting of
(1) statin compounds,
(2) casein kinase 1 inhibitors,
(3) cAMP inducers, and
(4) histone methyltransferase inhibitors,
to convert the somatic cells into osteoblasts.

Item 2. The method according to Item 1, wherein the somatic cells are fibroblasts, gingival cells, or adipocytes.

Item 3. The method according to Item 1 or 2, wherein the medium is an osteoblast induction medium.

Item 4. An inducer for inducing differentiated somatic cells into osteoblasts, the inducer comprising at least one compound selected from the group consisting of
(1) statin compounds,
(2) casein kinase 1 inhibitors,
(3) cAMP inducers, and
(4) histone methyltransferase inhibitors.

Item 5. A kit for inducing differentiated somatic cells into osteoblasts, the kit comprising:
at least one compound selected from the group consisting of
(1) statin compounds,
(2) casein kinase 1 inhibitors,
(3) cAMP inducers, and
(4) histone methyltransferase inhibitors; and
a medium.

Item 6. The kit according to Item 5, wherein the medium is an osteoblast induction medium.

Advantageous Effects of Invention

The present invention is capable of providing osteoblasts from differentiated somatic cells within a short period of time by the effect of a low-molecular-weight compound. These osteoblasts are easily induced from somatic cells of a subject into which the osteoblasts are to be transplanted; thus, even when osteoblasts themselves or bone tissue prepared therefrom are transplanted, immunological rejection or other problems do not occur. Further, osteoblasts may be directly induced from somatic cells without passing through iPS cells or ES cells, which avoids problems attributed to pluripotent stem cells, such as oncogenesis. Additionally, osteoblasts may be prepared and banked beforehand, and used for allotransplantation or xenotransplantation into patients.

DESCRIPTION OF EMBODIMENTS

Figure 1:
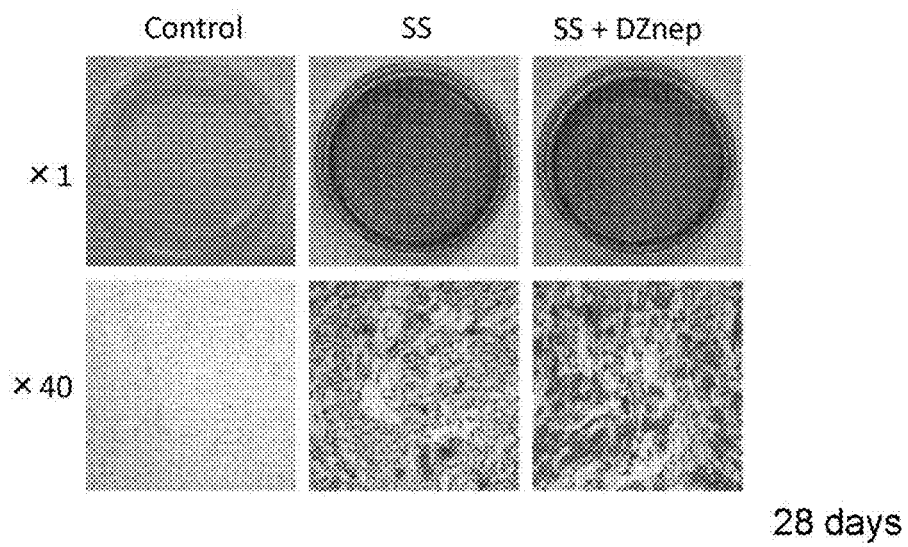
FIG. 1 shows Alizarin Red S staining images (28 days).

The present invention is characterized by obtaining osteoblasts from differentiated somatic cells by using a differentiated somatic cell medium in the presence of at least one low-molecular-weight compound selected from the group consisting of (1) statin compounds, (2) casein kinase inhibitors, (3) cAMP inducers, and (4) histone methyltransferase inhibitors.

The differentiated somatic cells to be directly reprogrammed into osteoblasts in the method of the present invention are not particularly limited as long as osteoblasts are excluded. Examples include fibroblasts, keratinocytes, oral mucosal epithelial cells, respiratory mucosal epithelial cells, gastric mucosal epithelial cells, intestinal mucosal epithelial cells, vascular endothelial cells, smooth muscle cells, adipocytes, gingival cells (gingival fibroblasts and gingival epithelial cells), leukocytes, lymphocytes, muscle cells, conjunctival epithelial cells, and osteoclasts, with fibroblasts, keratinocytes, oral mucosal epithelial cells, gingival cells, leukocytes, lymphocytes, osteoclasts, adipocytes, and the like being preferable.

In the method of the present invention, other compounds may further be used in combination to promote direct reprogramming into osteoblasts. Examples of such compounds include (i) low-molecular-weight compounds that promote iPS cell induction or cell reprogramming, (ii) compounds that induce Oct4, and (iii) epigenetic modifiers such as methyltransferase inhibitor, histone demethylase inhibitor, and histone deacetylase inhibitor.

The statin compounds widely encompass HMG-CoA reducing enzyme inhibitors. Examples include, but are not particularly limited to, simvastatin, atorvastatin, lovastatin, fluvastatin, pravastatin, cerivastatin, pitavastatin, rosuvastatin, dihydrocompactin, compactin, bervastatin, carbastatin, crilvastatin, dalvastatin, glenvastatin, fluindostatin, velostatin, mevastatin, rivastatin, cirivastatin, CI-981, and the like. Statin compounds to be developed in the future are all encompassed by the statin compounds of the present invention.

While not a limitation of the present invention, the statin compounds are believed to promote direct reprogramming into osteoblasts, in particular, through, for example, an increase in the expression level of Runx2 gene. The statin compounds are also believed to contribute to the promotion of calcium deposition.

The casein kinase inhibitors widely encompass inhibitors against casein kinases with subtypes, such as casein kinase 1 and casein kinase 2. In a preferable embodiment, a casein kinase 1 inhibitor may be used, from the viewpoint of high effect on the induction of osteoblasts.

Preferable examples of the casein kinase 1 inhibitors include D4476, IC261, CK1-7, A3, SB-431542, DRB, hymenialdisine, matairesinol, 5-iodotubercidin, meridianin, SB-203580, and other compounds (including compounds that specifically inhibit casein kinase 1).

Examples also include other compounds that inhibit casein kinase 1, such as fasudil, hydroxyfasudil, fenretinide, PKZ-ζ peptide pseudosubstrate, dimethyl sphingosine, CVS-3989, AG1024, 648450, K252a, C3 transferase, 553502, LY333531, ruboxistaurin, Go-6976, IWR-1-endo (IWR1e), and IWP-2.

Examples of the casein kinase 2 inhibitor include CX-4945.

As the casein kinase 1 inhibitor, derivatives of the above compounds may also be used in place of the above compounds. It is not always necessary for the derivatives to have activities to inhibit casein kinases. For example, a derivative of D4476 represented by the following formula (I) disclosed in WO 00/61576 may be used, in place of D4476 (4-[4-(2,3-dihydro-1,4-benzodioxin-6-yl)-5-(2-pyridinyl)1H-imidazol-2-yl]-benzamide), which is a casein kinase 1 inhibitor.

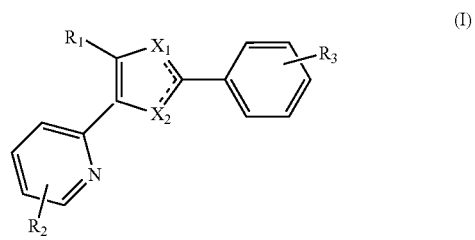

In the formula, $R_1$ is naphthyl, anthracenyl, or phenyl, each having at least one substituent selected from the group consisting of halogen, $C_{1-6}$ alkoxy (—O—$C_{1-6}$ alkyl), $C_{1-6}$ alkylthio (—S—$C_{1-6}$ alkyl), $C_{1-6}$ alkyl, —O—$(CH_2)_n$-Ph, —S—$(CH_2)_n$-Ph, cyano, phenyl (Ph), and $CO_2R$ (wherein R is hydrogen or $C_{1-6}$ alkyl, and n is 0, 1, 2, or 3); or
$R_1$ is phenyl fused with a 5- to 7-membered aromatic or non-aromatic ring optionally containing up to two heteroatoms independently selected from N, O, and S;
$R_2$ is H, $NH(CH_2)_n$-Ph, or NH—$C_{1-6}$ alkyl (wherein n is 0, 1, 2, or 3);
$R_3$ is $CO_2H$, $CONH_2$, CN, $NO_2$, $C_{1-6}$ alkylthio, —$SO_2$—$C_{1-6}$ alkyl, $C_{1-6}$ alkoxy, $SONH_2$, CONHOH, $NH_2$, CHO, $CH_2OH$, $CH_2NH_2$, or $CO_2R$ (wherein R is hydrogen or $C_{1-6}$ alkyl);
one of $X_1$ and $X_2$ is N or CR', and the other is NR' or CHR' (wherein R' is hydrogen, OH, $C_{1-6}$ alkyl, or $C_{3-7}$ cycloalkyl) or;
when one of $X_1$ and $X_2$ is N or CR', the other may be S or O.

Examples of $C_{1-6}$ alkyl include straight or branched chain $C_{1-6}$ alkyl, such as methyl, ethyl, n-propyl, isopropyl, n-butyl, isobutyl, sec-butyl, tert-butyl, n-pentyl, isopentyl, n-hexyl, and isohexyl.

Examples of $C_{3-7}$ cycloalkyl include $C_{3-7}$ cyclopropyl, such as cyclopropyl, cyclobutyl, cyclopentyl, cyclohexyl, and cycloheptyl.

When $R_1$ is phenyl fused with a 5- to 7-membered aromatic or non-aromatic ring optionally containing up to two heteroatoms independently selected from N, O, and S, specific examples include benzo[1,3]dioxolyl, 2,3-dihydrobenzo[1,4]dioxynyl, benzoxazolyl, benzothiazolyl, benzo[1,2,5]oxadiazolyl, benzo[1,2,5]thiadiazolyl, and dihydrobenzofuranyl.

Examples of such derivatives of D4476 include the following compounds:
4-[4-(4-fluorophenyl)-5-(2-pyridyl)-1-hydroxy-1H-imidazol-2-yl]benzonitrile;
4-[4-(4-fluorophenyl)-5-(2-pyridyl)-1H-imidazol-2-yl]benzonitrile;
4-[4-(4-fluorophenyl)-5-(2-pyridyl)-1H-imidazol-2-yl]benzoic acid;
4-[4-(4-fluorophenyl)-5-(2-pyridyl)-1H-imidazol-2-yl] methyl benzoate;
4-[4-(4-fluorophenyl)-5-(2-pyridyl)-1H-imidazol-2-yl]ethyl benzoate;
4-(4-benzo[1,3]dioxol-5-yl-1-hydroxy-5-pyridin-2-yl-1H-imidazol-2-yl)benzonitrile;
4-(4-benzo[1,3]dioxol-5-yl-5-pyridin-2-yl-1H-imidazol-2-yl)benzonitrile;
4-benzo[1,3]dioxol-5-yl-5-pyridin-2-yl-1H-imidazol-2-yl)benzoic acid;
2-[4-benzo[1,3]dioxol-5-yl-2-(4-nitrophenyl)-1H-imidazol-5-yl]pyridine;

3-(4-benzo[1,3]dioxol-5-yl-5-pyridin-2-yl-1H-imidazol-2-yl)phenylamine;

4-[4-(4-fluorophenyl)-2-(4-nitrophenyl)-1H-imidazol-5-yl]pyridine;

4-[4-(4-fluorophenyl)-5-pyridin-2-yl-1H-imidazol-2-yl phenylamine;

4-(4-benzo[1,3]dioxol-5-yl-5-pyridin-2-yl-1H-imidazol-2-yl)phenyl]methanol;

4-(4-benzo[1,3]dioxol-5-yl-5-pyridin-2-yl-1H-imidazol-2-yl)benzamide;

4-[4-(2,3-dihydro-benzo[1,4]dioxin-6-yl)-5-pyridin-2-yl-1H-imidazol-2-yl]-benzonitrile;

4-[4-(2,3-dihydro-benzofuran-5-yl)-5-pyridin-2-yl-1H-imidazol-2-yl]benzamide;

3-[4-benzo[1,3]dioxol-5-yl-5-pyridin-2-yl-1H-imidazol-2-yl)benzonitrile;

4-[4-(2,3-dihydro-benzofuran-6-yl)-5-pyridin-2-yl-1H-imidazol-2-yl]benzonitrile;

4-[4-(2,3-dihydro-benzofuran-6-yl)-5-pyridin-2-yl-1H-imidazol-2-yl]benzamide;

3-(4-benzo[1,3]dioxol-5-yl-5-pyridin-2-yl-1H-imidazol-2-yl)benzoic acid;

4-[4-(4-methoxyphenyl)-5-(2-pyridyl)-1H-imidazol-2-yl]benzonitrile;

4-[4-(2,2-difluoro-benzo[1,3]dioxol-5-yl)-5-pyridin-2-yl-1H-imidazol-2-yl]benzamide;

4-[4-(2,3-dihydro-benzo[1,4]dioxin-6-yl)-1-methyl-5-pyridin-2-yl-1H-imidazol-2-yl]benzamide;

4-[5-(2,3-dihydro-benzo[1,4]dioxin-6-yl)-1-methyl-4-pyridin-2-yl-1H-imidazol-2-yl]benzamide;

4-(5-benzo[1,3]dioxol-5-yl-4-pyridin-2-yl-oxazol-2-yl)benzonitrile;

4-(5-benzo[1,3]dioxol-5-yl-4-pyridin-2-yl-oxazol-2-yl)benzamide; and 4-(4-benzo[1,3]dioxol-5-yl-5-pyridin-2-yl-1H-pyrrol-2-yl)benzamide.

While not a limitation of the present invention, the casein kinase 1 inhibitors are believed to promote direct reprogramming into osteoblasts, in particular, through, for example, an increase in the expression level of ALP (alkaline phosphatase) and promotion of calcium deposition.

The cAMP inducers (may also be referred to as adenylate cyclase activating agents) widely encompass compounds that increase the intracellular cAMP (cyclic AMP) level with the activation of adenylate cyclase. Examples include forskolin (FRK), isoproterenol, and the like.

While not a limitation of the present invention, the cAMP inducers are believed to promote direct reprogramming into osteoblasts, in particular, through, for example, an increase in the expression level of Runx2 gene. The cAMP inducers are also believed to contribute to promotion of calcium deposition.

Examples of the histone methyltransferase inhibitors include DZNep (3-deazaneplanocin A), BIX-01294, and the like.

While not a limitation of the present invention, the cAMP inducers are believed to promote direct reprogramming into osteoblasts, in particular, through, for example, the promotion of calcium deposition.

The concentration of the statin compound in the medium is not particularly limited as long as induction of osteoblasts is possible, and is, for example, about 100 pM to 10 µM, preferably about 500 pM to 5 µM, more preferably about 1 nM to 1 µM, and still more preferably about 10 to 100 nM.

The concentration of the casein kinase 1 inhibitor in the medium is not particularly limited as long as induction of osteoblasts is possible, and is, for example, about 0.01 to 100 µM, preferably about 0.1 to 50 µM, and more preferably about 1 to 10 µM.

The concentration of the cAMP inducer in the medium is not particularly limited as long as induction of osteoblasts is possible, and is, for example, about 0.01 to 100 µM, preferably about 0.1 to 50 µM, and more preferably about 1 to 10 µM.

The concentration of the histone methyltransferase inhibitor in the medium is not particularly limited as long as induction of osteoblasts is possible, and is, for example, about 100 pM to 50 µM, preferably about 1 nM to 10 µM, more preferably about 5 nM to 1 µM, and still more preferably about 10 to 100 nM.

The low-molecular-weight compounds incorporated in the medium may be used alone, or in a combination of two or more. The combination is not particularly limited when two or more different low-molecular-weight compounds are used in combination. From the viewpoint of high effect on the induction of osteoblasts, a combination of, for example, a statin compound and a casein kinase 1 inhibitor is preferable. It is certainly possible to further combine a cAMP inducer and/or a histone methyltransferase inhibitor with the statin compound and casein kinase 1 inhibitor combination.

When two or more different low-molecular-weight compounds are used in combination, the two or more low-molecular-weight compounds may be used together during the culture, or a different low-molecular-weight compound (or compounds) may be used per each part of the culture. It is also possible to mix cells cultured with the addition of one or more low-molecular-weight compounds with cells cultured with the addition of other one or more low-molecular-weight compounds.

The medium for inducing osteoblasts is not particularly limited, and is preferably an induction medium. Examples of the induction medium include general-purpose liquid media (e.g., DMEM (Dulbecco's Modified Eagle's Medium) and EMEM (Eagle's Minimal Essential Medium)) to which ascorbic acid; β-glycerophosphate; at least one member selected from the group consisting of glucocorticoids, such as dexamethasone and hydrocortisone; serum components (e.g., fetal bovine serum (FBS) and human serum (HS)); antibiotics, such as streptomycin; and the like are added. More specific examples include general-purpose media, such as DMEM, to which 50 µG/ml ascorbic acid, 10 mM β-glycerophosphate, 100 nM dexamethasone (all of the concentrations are final concentrations), and 10% FBS or 5% HS, and optionally 1% antibiotic and 1% NEAA (nonessential amino acids) are added.

The culture temperature is about 37° C. The culture period is about 1 to 6 weeks, preferably 2 to 5 weeks, and more preferably 3 to 4 weeks.

For the medium, a solvent, such as DMSO, may also be used.

The kit of the present invention comprises an osteoblast medium and a statin compound, and optionally a casein kinase inhibitor, a histone methyltransferase inhibitor, and the like.

The present invention enables the preparation of preosteoblasts, immature osteoblasts, mature osteoblasts, bone cells, and the like. In this specification, for expediency, all of these cells are referred to as "osteoblasts."

Examples of diseases to be treated with osteoblasts (transplantation material) obtained by the present invention include bone defects due to bone tumors, trauma, osteomyelitis, and the like, bone defects after curettage of bone tumors and the like, bone fracture, osteoporosis, periodontal disease, alveolar bone resorption, rheumatoid arthritis, idiopathic osteonecrosis of the femoral head, arthrosis deformans, lumbar spondylosis deformans, spinal canal stenosis, disc herniation, spondylolysis, spondylolytic spondylolisthesis, scoliosis, cervical spondylotic myelopathy, ossification of posterior longitudinal ligament, spinal cord injury, coxarthrosis, gonarthrosis, capital femoral epiphysis, osteomalacia, reconstruction at a bone fracture site destroyed by complex fracture, such as lower jaw reconstruction, repair of bone after surgery (repair of breast bone after cardiac surgery), repair of a defect site associated with artificial ankle joint surgery, osteomyelitis, osteonecrosis, and the like. Further, when the osteoblasts are transplanted in combination with transplantation of bone, transplantation of artificial bone, and use of artificial joint, or implant, therapeutic effects may be enhanced. Additionally, when bone tissues prepared in vitro by culturing osteoblasts using a three-dimensional scaffold or the like so as to have various shapes are transplanted, the above-mentioned diseases can be treated. In addition to the diseases, various diseases involved in loss, lack, or decreased function of osteoblasts are targeted.

In this specification, unless otherwise specified, the term "treatment" refers to treatment for a patient suffering from a specific disease or disorder, and means to ameliorate the severity of the disease or disorder, ameliorate one or more symptoms thereof, or delay or reduce the speed of progress of the disease or disorder. In this specification, the "treatment" includes "prevention."

The osteoblasts obtained in the present invention may be used not only for treatment of a disease, but also for beauty. For example, when the osteoblasts or bone tissue formed of the osteoblasts are transplanted to a defect site associated with an accident, surgery, or the like, the cells can produce a bone matrix to repair the defect site and to obscure the defect site by three-dimensional repair. In such a case, for expediency, treatment for humans is also referred to as treatment in this specification. The term "patient" may be replaced by the term "healthy subject" or "human," and the term "disease" may be replaced by the term "beauty."

The present invention can also be used not only for treatment for diseases of humans, but also for treatment for diseases of mammals including pets, such as dogs and cats; and livestock, such as cattle, horses, swine, sheep, and chickens. In such a case, the term "patient" may be replaced by the term "livestock" or "mammal."

The transplantation material refers to an osteoblast-containing material to be introduced into a living body for repair and reconstruction of bone tissue. The transplantation material includes a material that partially or completely regenerates bone tissue in vitro, and is transplanted to the same or another individual. The osteoblasts obtained in the present invention can be used for preparation of the transplantation material. The osteoblasts themselves may also be used as the transplantation material. Accordingly, the osteoblasts may be transplanted to a patient as a cell preparation; transplanted together with a base (scaffold) formed of an artificial material, such as hydroxyapatite or bioabsorbable ceramic; or cultured with a scaffold and then transplanted. In such case, the scaffold may form various three-dimensional shapes depending on the purpose of transplantation.

The somatic cells may be derived from mammals. When osteoblasts are transplanted to a living body, somatic cells (autologous cells) derived from a test subject who undergoes transplantation are preferably used to reduce risks of infection, rejection responses, and the like. However, instead of the autologous cells, osteoblasts prepared beforehand from somatic cells of another person or another animal may be used for, for example, transplantation for sudden bone fracture or the like. Alternatively, osteoblasts may be prepared from somatic cells of another person or another animal prepared beforehand, and used for transplantation. That is, an osteoblast bank or an osteoblast precursor cell bank may be prepared beforehand and used for transplantation. In such a case, in order to reduce risks, such as rejection responses, MHC typing may be carried out beforehand. Further, characteristics and tumorigenicity of osteoblasts may be confirmed beforehand.

In this specification, examples of the mammal include mice, rats, hamsters, humans, dogs, cats, monkeys, rabbits, cattle, horses, and swine, and particularly humans.

The present invention can also be used for, for example, various studies and development of technologies using osteoblasts. For example, the present invention is useful for basic studies such as analysis of osteogenesis, bone aging, morphogenesis, mechanisms of remodeling, mechanical stress against the factors, and influences of nutrients, immunity, nerves, and hormones. The present invention is also useful for, for example, analysis of the influence of internal exposure to a radioactive substance, such as strontium-90, on bone, and development of a technology for removing strontium-90 from bone.

The use of the present invention allows osteoblasts to be established from humans or animals having various diseases or genetic backgrounds in a simple, rapid, and inexpensive manner. Accordingly, abnormalities in osteoblasts related to the diseases or genetic backgrounds can be analyzed by, for example, a biochemical, molecular biological, or immunological technique. This can contribute to studies on clarification of pathogenic mechanisms of diseases and the like, or development of diagnostic methods. Development of drugs, toxicity tests of drugs, and the like using such osteoblasts can contribute to the development of novel treatment methods for various diseases.

Whether osteoblasts were obtained can be confirmed by, for example, the measurement of mRNA of ALP (alkaline phosphatase), osteocalcin (OC), osteopontin, or Runx2 using real-time PCR, or by Alizarin Red S staining (production of calcified bone matrix).

Runx2 is an essential transcription factor in bone formation. Runx2 plays an indispensable role in in vivo differentiation of mesenchymal stem cells into osteoblasts. Enforced expression of Runx2 in mesenchymal stem cells increase osteoblast-specific genes, such as OC (osteocalcin), BSP (bone sialo-protein), ALP (alkaline phosphatase), and COL1A1. In Runx2 knockout mice, intramembranous ossification or endochondral ossification never occurs due to the loss of mature osteoblasts; however, mesenchymal stem cells of this mouse are capable of being induced into adipocytes and chondrocytes.

ALP (alkaline phosphatase) is an early- to mid-stage osteoblast differentiation marker. ALP is contained in a large amount in the membrane surface of osteoblasts and in matrix vesicles secreted from osteoblasts, and is involved in the initiation of calcified matrix production.

Osteocalcin (OC) is specifically expressed in osteoblasts, and is believed to contribute to the promotion of bone formation.

Alizarin Red S staining and von Kossa staining can detect the production of calcified bone matrix, i.e., calcium deposition, which is one of the important elements for bone formation.

EXAMPLES

Examples are shown below. However, the present invention is not limited to only these Examples.

Example 1

1-1: Alizarin Red S Staining (FIG. 1)

A normal human dermal fibroblast (HDF) strain was seeded in a 35-mm culture dish at a concentration of $5 \times 10^4$ cells/well, and cultured under standard conditions in an induction medium to which 100 nM simvastatin (SS), or 100 nM simvastatin (SS) and 1 µM DZNep had been added. The composition of the induction medium is as follows: 50 µg/ml ascorbic acid, 10 mM β-glycerophosphate, 100 nM dexamethasone (all of the concentrations are final concentrations), 10% FBS, 1% antibiotic, 1% NEAA, and α-MEM. The standard conditions refer to 37° C., 5% $CO_2$, and 95% humidified air. The medium was replaced about once every four days, and culture was performed for 28 days. The culture medium was removed by aspiration from the culture dish, and the cells were washed twice with distilled water, followed by fixation with 10% formalin. After washing was performed with sterile distilled water, an Alizarin Red S staining solution was added thereto, followed by still standing at room temperature for 20 minutes. The cells were washed with sterile distilled water, and then observed with the naked eye and under a microscope. FIG. 1 shows the results. Calcified bone matrix is shown as red staining. This indicates that the addition of SS or the addition of SS and DZNep converted fibroblasts into osteoblasts, which produce a large amount of calcified bone matrix.

Figure 2:
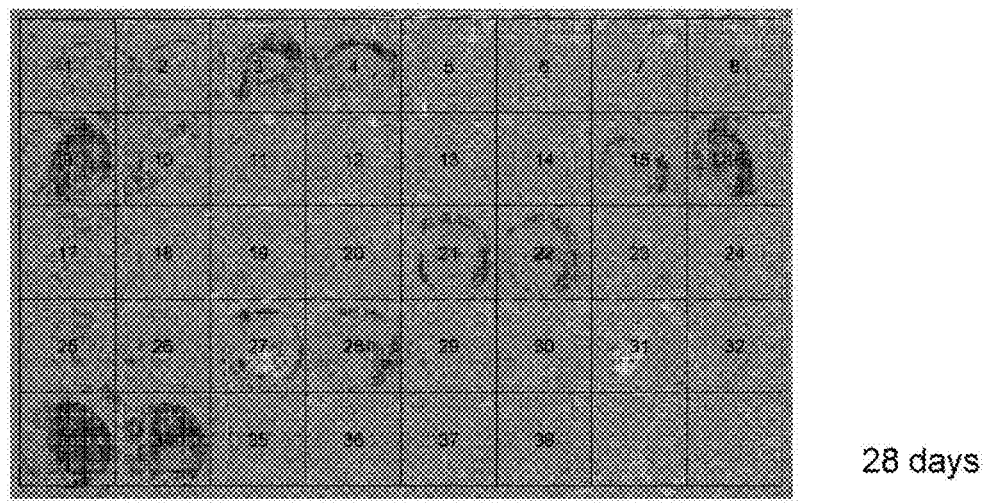
FIG. 2 shows Alizarin Red S staining images (28 days).
Figure 3:
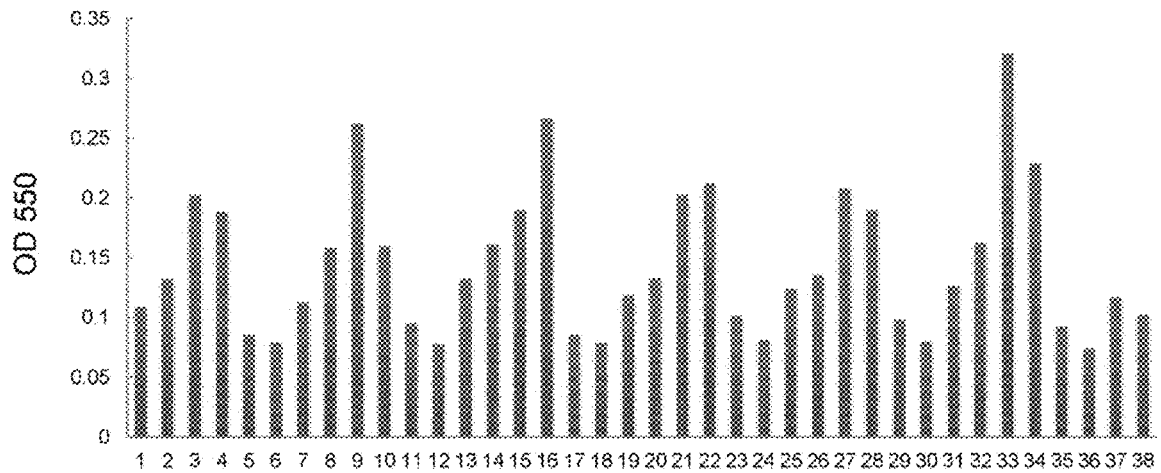
FIG. 3 shows Alizarin Red S staining intensity.

1-2: Alizarin Red S Staining (FIGS. 2 and 3)

A normal human dermal fibroblast (HDF) strain was seeded in a 24-well plate, and cultured under standard conditions in an induction medium to which 100 nM simvastatin (SS), hydroxycortisone at various concentrations, and β-glycerophosphate at various concentrations had been added (in the table, "O" indicates each concentration of the compound added). The medium was replaced about once every four days, and culture was performed for 28 days. The culture medium was removed by aspiration from the plate, and the cells were washed twice with distilled water, followed by fixation with 10% formalin. After washing was performed with sterile distilled water, an Alizarin Red S staining solution was added thereto, and then left to stand at room temperature. After 20 minutes, the staining reaction solution was collected. Thereafter, the cells were washed with sterile distilled water, and then observed with the naked eye and under a microscope. FIG. 2 shows the results. Further, the absorbance (550 nm) of the staining reaction solution collected from each well was measured using a microplate reader. FIG. 3 shows the results. It is clarified that 100 nM simvastatin (SS) in the presence of hydroxycortisone and β-glycerophosphate converts fibroblasts into osteoblasts, and that at this time, hydroxycortisone is preferably at a concentration of 125 to 4000 nM, and β-glycerophosphate is preferably at a concentration of 10 to 20 µM.

Figure 4:
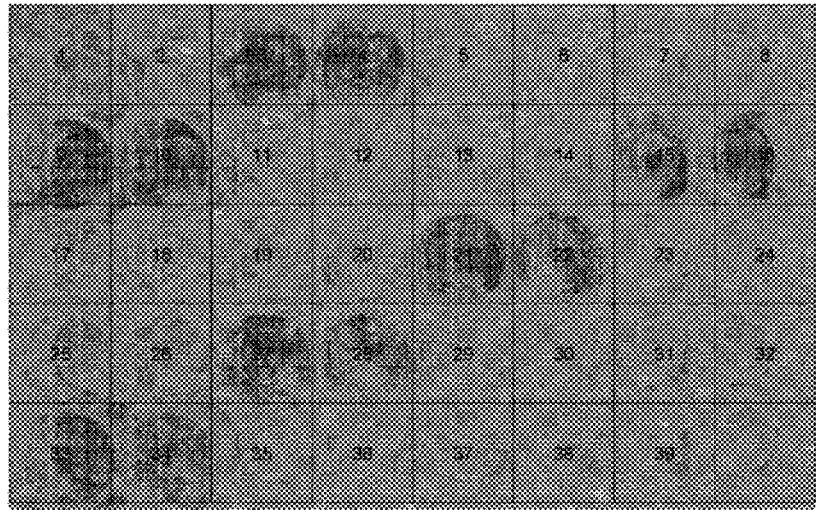
FIG. 4 shoes Alizarin Red S staining images (28 days).
Figure 5:
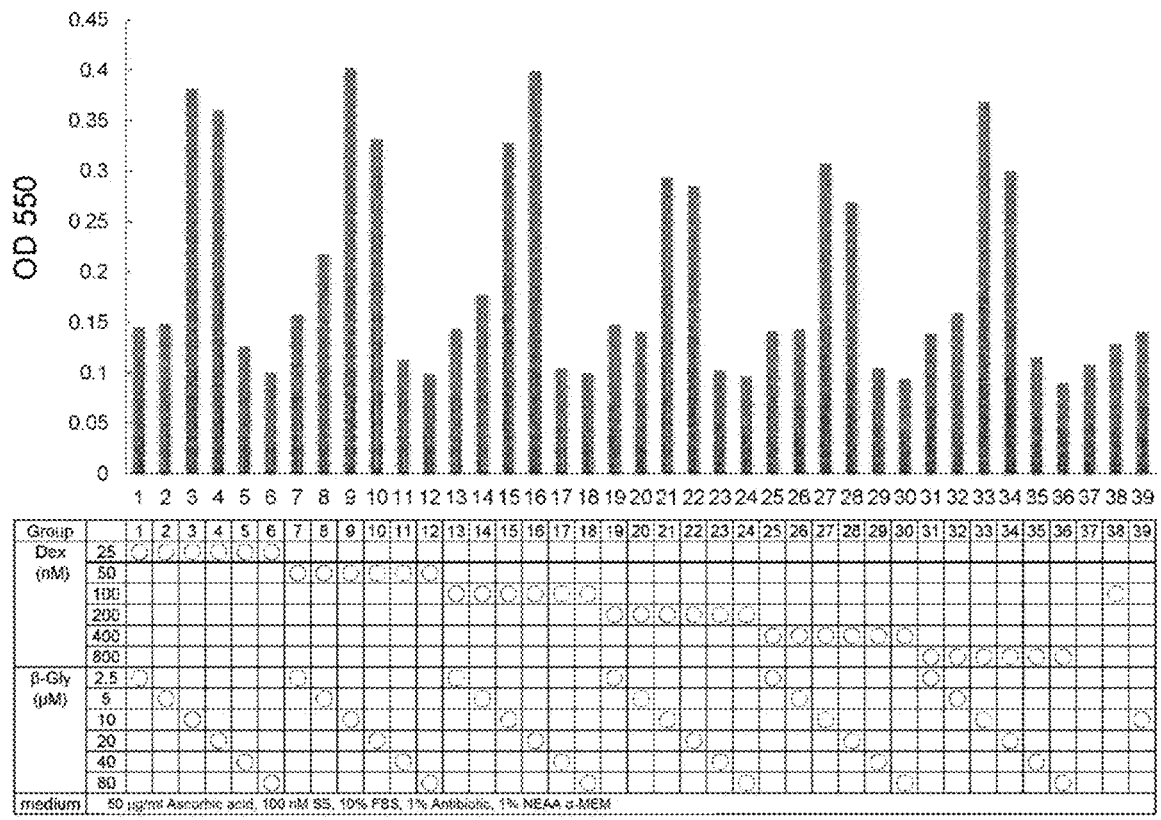
FIG. 5 shows Alizarin Red S staining intensity.

1-3: Alizarin Red S Staining (FIGS. 4 and 5)

A normal human dermal fibroblast (HDF) strain was seeded in a 24-well plate, and cultured under standard conditions in an induction medium to which 100 µM simvastatin (SS), dexamethasone (Dex) at various concentrations, and β-glycerophosphate at various concentrations had been added (in the table, "O" indicates each concentration of the compound added). The medium was replaced about once every four days, and culture was performed for 28 days. The culture medium was removed by aspiration from the plate, and the cells were washed twice with distilled water, followed by fixation with 10% formalin. After washing was performed with sterile distilled water, an Alizarin Red S staining solution was added thereto, and then left to stand at room temperature. After 20 minutes, the staining reaction solution was collected. Thereafter, the cells were washed with sterile distilled water, and then observed with the naked eye and under a microscope. FIG. 4 shows the results. Further, the absorbance (550 nm) of the staining reaction solution collected from each well was measured using a microplate reader. FIG. 5 shows the results. It is clarified that 100 nM simvastatin (SS) in the presence of dexamethasone and β-glycerophosphate induces fibroblasts into osteoblasts, and that at this time, dexamethasone is preferably at a concentration of 25 to 800 nM, and β-glycerophosphate is preferably at a concentration of 10 to 20 µM.

Figure 6:
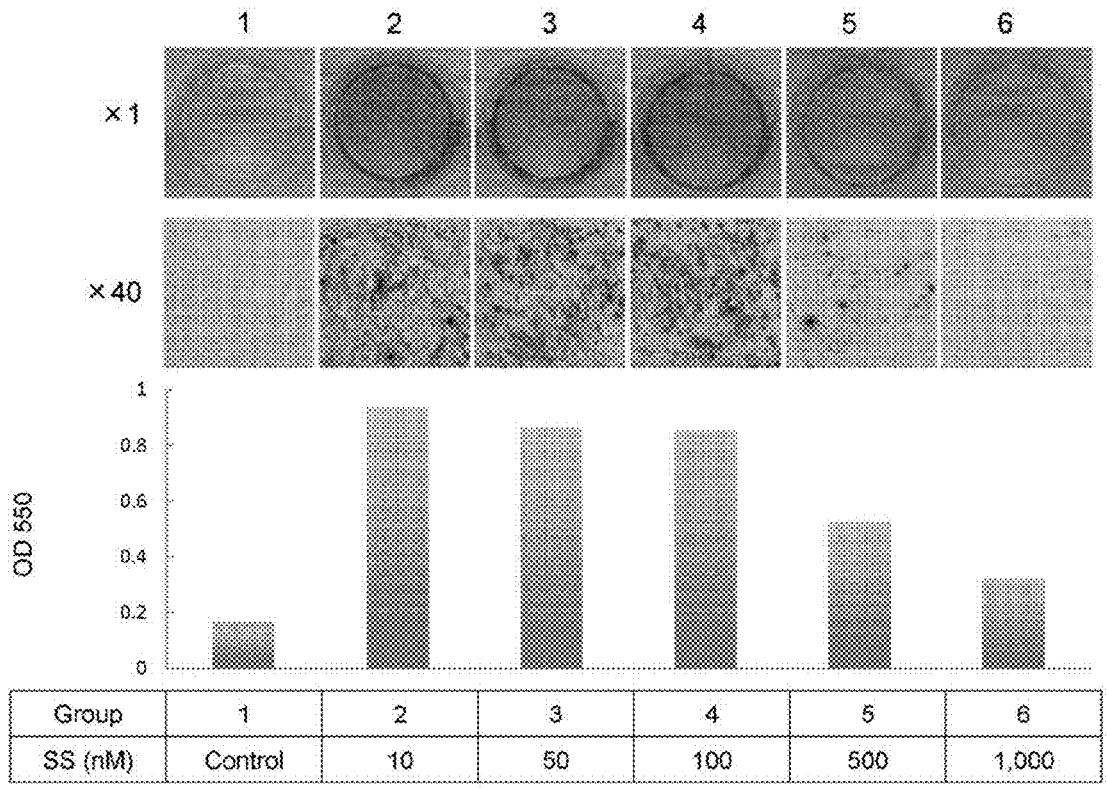
FIG. 6 shows Alizarin Red S staining images and intensity.

1-4: Alizarin Red S Staining (FIG. 6)

A normal human dermal fibroblast (HDF) strain was seeded in a 24-well plate, and cultured under standard conditions in an induction medium to which simvastatin (SS) at various concentrations had been added. The medium was replaced about once every four days, and culture was performed for 28 days. The culture medium was removed by aspiration from the plate, and the cells were washed twice with distilled water, followed by fixation with 10% formalin. After washing was performed with sterile distilled water, an Alizarin Red S staining solution was added thereto, and then left to stand at room temperature. Twenty minutes later, the staining reaction solution was collected. Thereafter, the cells were washed with sterile distilled water, and then observed with the naked eye and under a microscope. Further, the absorbance (550 nm) of the collected staining reaction solution was measured using a microplate reader. FIG. 6 shows the results. It is clarified that the simvastatin concentration desirable for induction of osteoblasts is 10 to 100 nM.

Figure 7:
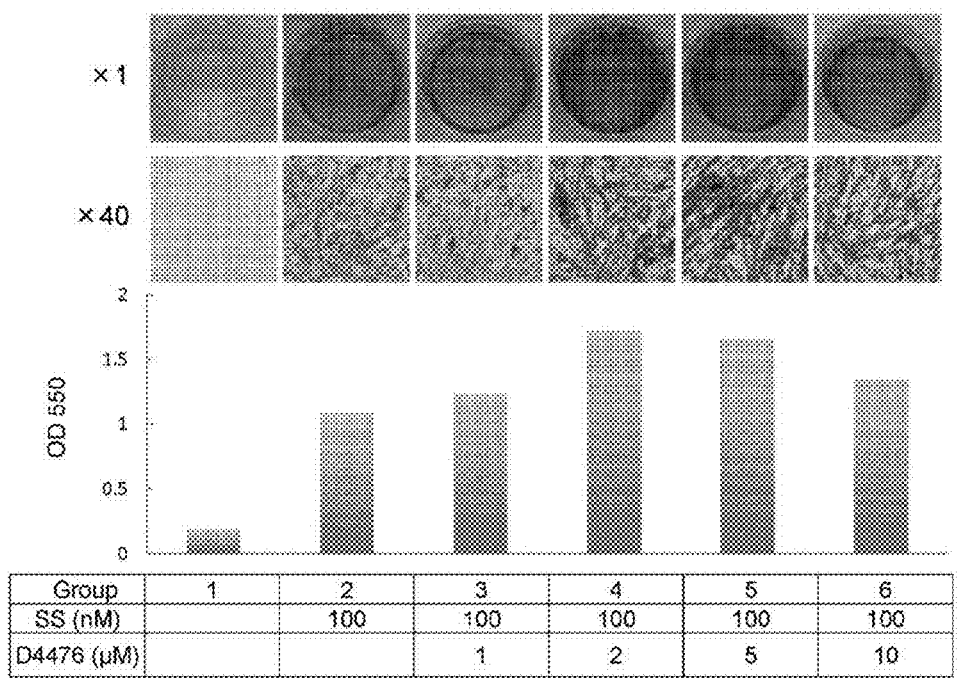
FIG. 7 shows Alizarin Red S staining images and intensity.

1-5: Alizarin Red S Staining (FIG. 7)

A normal human dermal fibroblast (HDF) strain was seeded in a 24-well plate, and cultured under standard conditions in an induction medium to which simvastatin (SS) and D4476 (casein kinase inhibitor) had been added at various concentrations. The medium was replaced about once every four days, and culture was performed for 28 days. Thereafter, the culture medium was removed by aspiration from the plate, and the cells were washed twice with distilled water, followed by fixation with 10% formalin. After washing was performed with sterile distilled water, an Alizarin Red S staining solution was added thereto, and then left to stand at room temperature. Twenty minutes later, the staining reaction solution was collected. Thereafter, the cells were washed with sterile distilled water, and then observed with the naked eye and under a microscope. Further, the absorbance (550 nm) of the collected staining reaction solution was measured using a microplate reader. FIG. 7 shows the results. It is clarified that 100 nM simvastatin in combination with 2 to 5 µM D4476 increases induction efficiency into osteoblasts.

Figure 8:
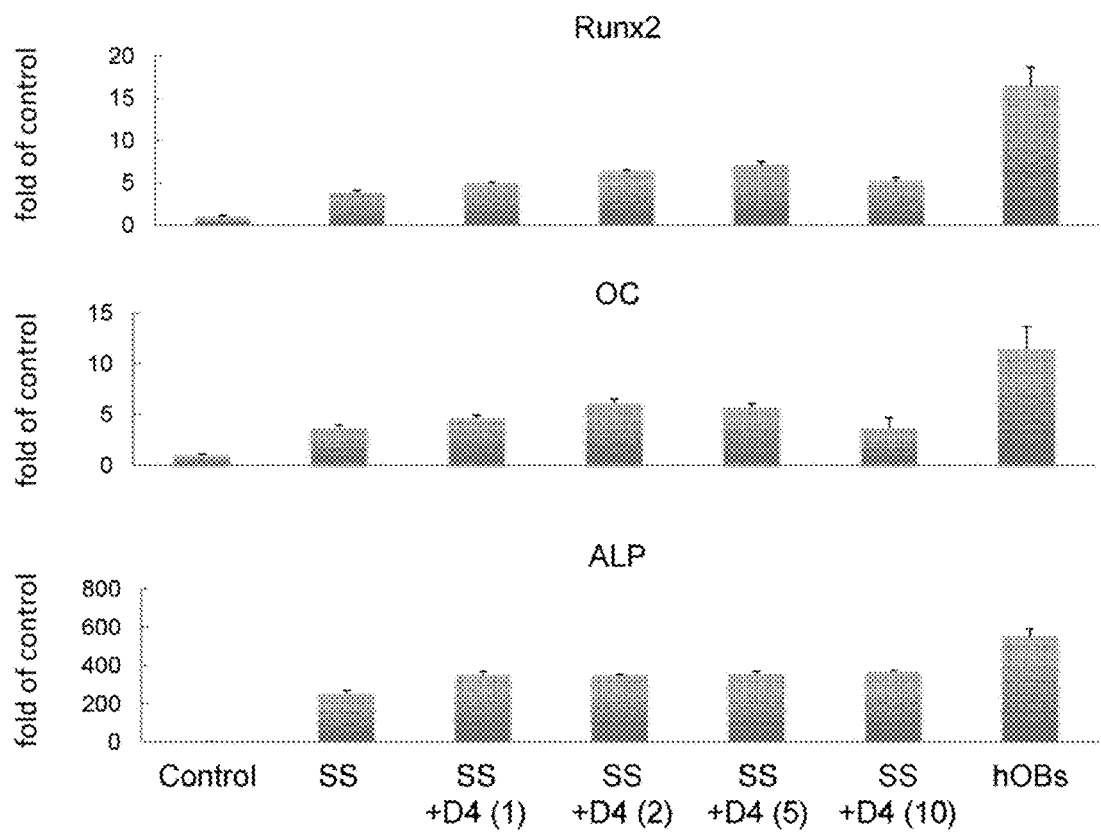
FIG. 8 shows mRNA expression levels of Runx2, Osteocalcin (OC), or ALP by real-time RT-PCR. In the figure, "FBs" represents fibroblasts, "OBs" represents osteoblasts, "SS" represents cells cultured with the addition of simvastatin, and "SS+D" represents cells cultured with the addition of simvastatin and D4476.

1-6: Real-Time RT-PCR (FIG. 8)

A normal human dermal fibroblast (HDF) strain was seeded in a 12-well plate, and cultured under standard conditions in an induction medium to which 100 nM simvastatin (SS) and D4476 (casein kinase inhibitor) at various concentrations had been added (the numerical numbers in parentheses are expressed in µM). The medium was replaced about once every four days, and culture was performed for 21 days. Then, total RNA was collected from the cells using ISOGEN II, and cDNA was synthesized using ReverTra Ace qPCR RT Master Mix. Real-time PCR Master Mix, TaqMan probes, specific primers, and cDNA were mixed, and real-time RT-PCR was performed using an AB7300 Real-Time PCR System to quantify the mRNA of Runx2, osteocalcin (OC), and alkaline phosphatase (ALP) genes. To use as a control, RNA was harvested from fibroblasts cultured without adding simvastatin, and the same analysis was performed. Further, RNA was harvested from human osteoblasts, and the same analysis was performed. FIG. 8 shows the results. The vertical axis shows relative values of mRNA of each gene, the values being obtained on the assumption that the mRNA level of the cells (control) is 1. It is clarified that osteoblasts induced from fibroblasts with the use of 100 nM simvastatin express Runx2, osteocalcin (OC), and alkaline phosphatase (ALP), and that a combined use of 2 to 5 μM D4476 achieves comparable or greater expression thereof.

Figure 9:
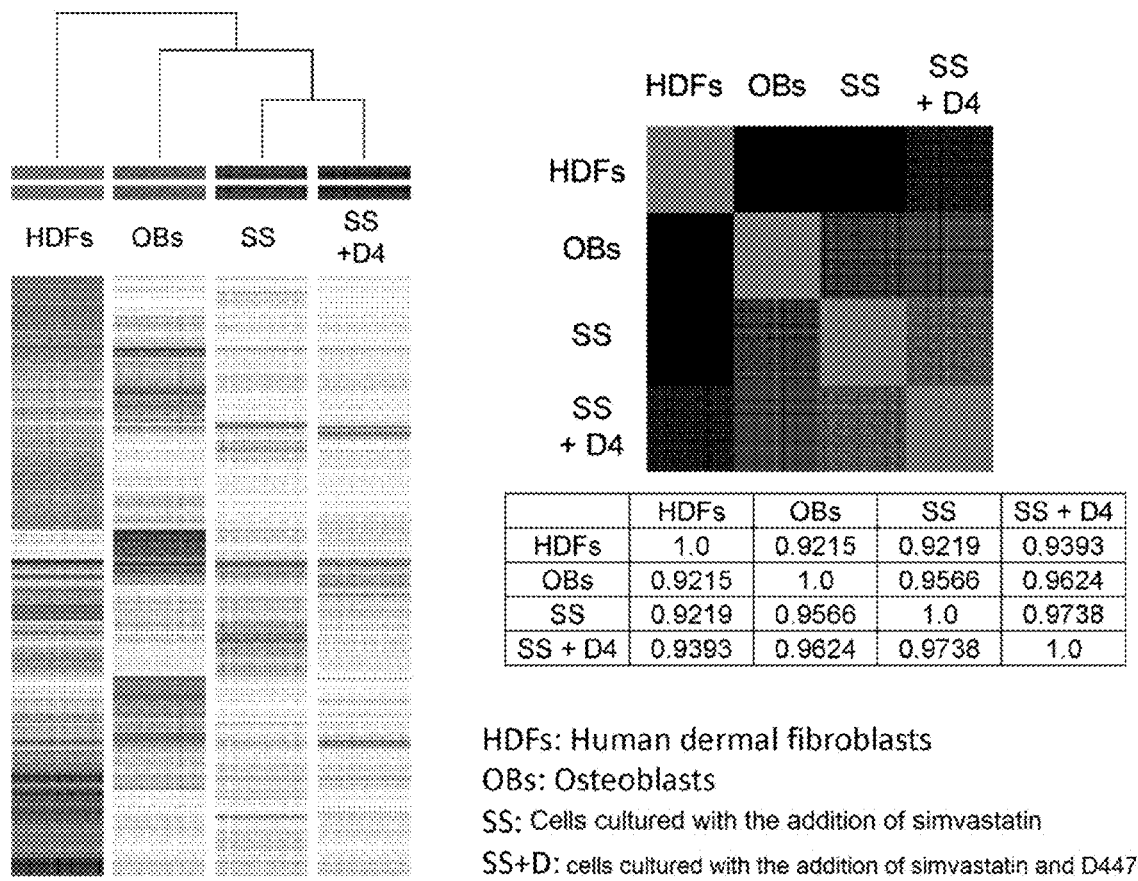
FIG. 9 shows the results of DNA microarray.

1-7: DNA Micro Array (FIG. 9)

A normal human dermal fibroblast (HDF) strain was seeded in a 60-mm culture dish, and cultured under standard conditions in an induction medium to which 100 nM simvastatin (SS), or 100 nM simvastatin (SS) and 2 μM D4476 (SS+D4) had been added. The medium was replaced about once every four days, and culture was performed for 21 days. Then, total RNA was collected from the cells using ISOGEN II. Similarly, total RNA was collected from human dermal fibroblasts (HDFs) and human osteoblasts (OBs). The mRNA expression pattern of each cell was analyzed genome-wide using a DNA chip of Affymetrix, Inc. FIG. 9 shows the results. Both "SS" and "SS+D4" showed global gene expression patterns similar to that of osteoblasts, rather than that of fibroblasts, and "SS+D4" showed a global gene expression pattern more similar to that of osteoblasts, compared to "SS."

Example 2

Figure 10:
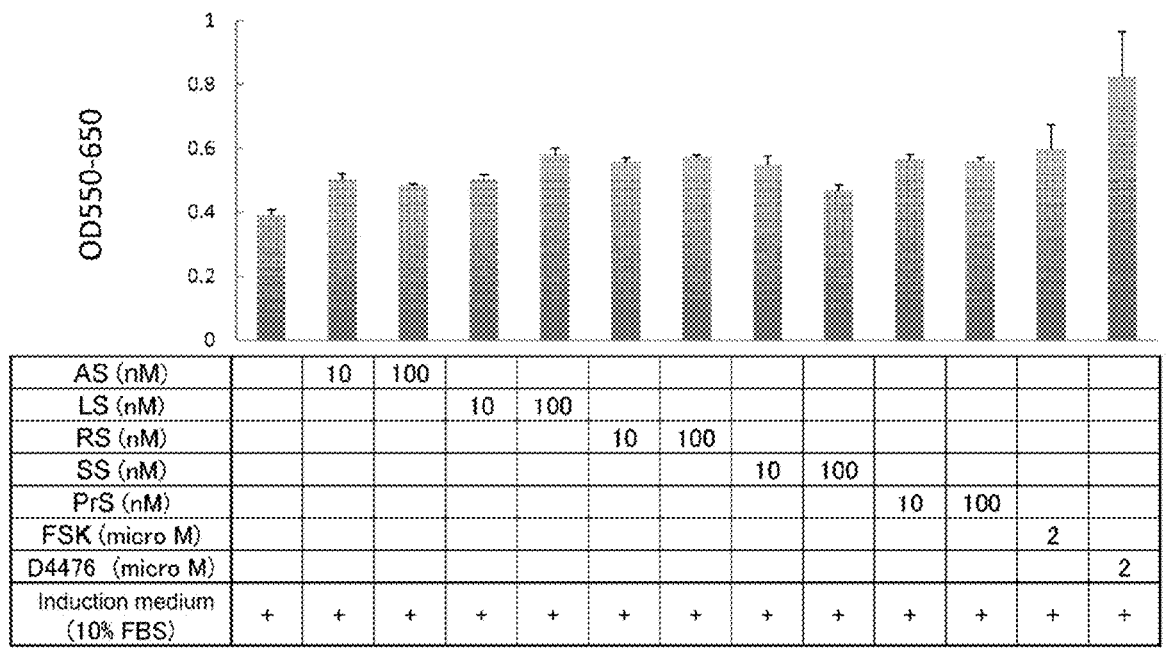
FIG. 10 shows Alizarin Red S staining intensity (28 days).

2-1: Alizarin Red S Staining (FIG. 10)

A normal human dermal fibroblast (HDF) strain was seeded in a 24-well plate at a concentration of $5 \times 10^3$ cells/well (day 0). On the next day, the culture medium was removed from each well and replaced with fresh medium (500 μl/well). The induction medium was obtained by adding 10% fetal bovine serum (FBS) to Dulbecco's Modified Eagle's Medium (DMEM), 50 μg/ml ascorbic acid, 10 mM β-glycerophosphate, and 100 nM dexamethasone. Further, the small molecular compounds were added as shown in the Figure. "AS" represents atorvastatin, "LS" represents lovastatin, "RS" represents rosuvastatin, "PiS" represents pitavastatin, "SS" represents simvastatin, "PrS" represents pravastatin, and "FSK" represents forskolin. "AS" was purchased from LKT Laboratories (St Paul, USA), "LS" was from Cayman Chemical (Ann Arbor, USA), "RS" was from Cayman Chemical (Ann Arbor, USA), "PiS" was from Cayman Chemical (Ann Arbor, USA), "SS" was from Sigma (St Louis, USA), "PrS" was from Cayman Chemical (Ann Arbor, USA), and "FSK" was from Sigma (St Louis, USA). The culture medium was replaced once every 3 to 4 days, and culture was performed.

The compounds used in this Example are shown below.

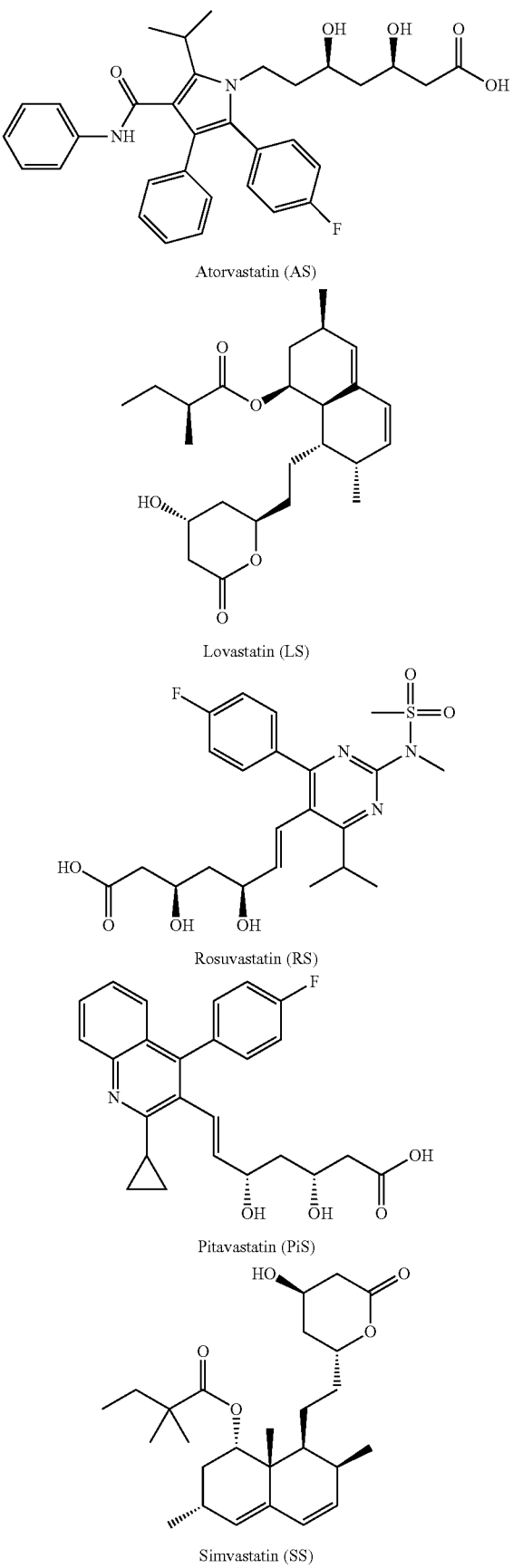

Atorvastatin (AS)

Lovastatin (LS)

Rosuvastatin (RS)

Pitavastatin (PiS)

Simvastatin (SS)

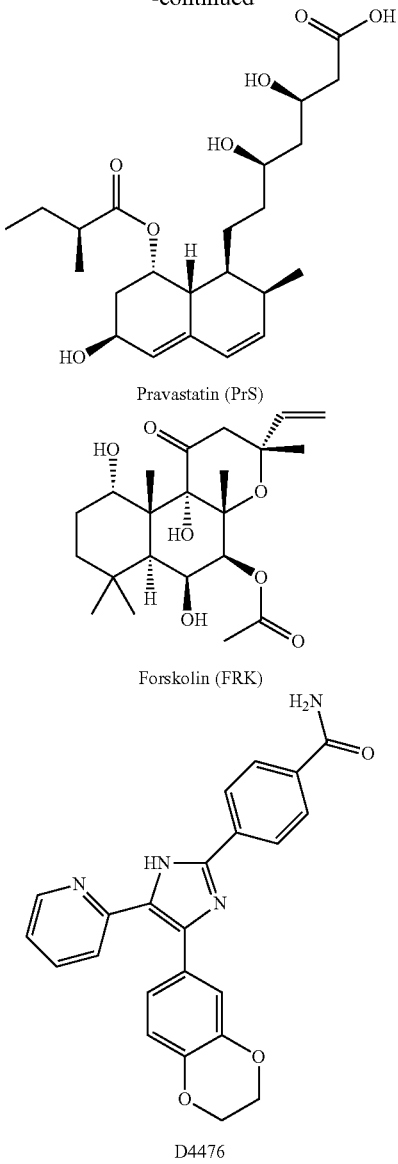

Pravastatin (PrS)

Forskolin (FRK)

D4476

Twenty-eight days after the culture, the culture medium was aspirated from each well, and the cells were washed with PBS (−), followed by fixation with 10% formalin. After washing was performed 3 times with sterile distilled water, an Alizarin Red-S staining solution was added, followed by incubation at room temperature for 15 minutes. The liquid was collected from each well, and transferred to a 96-well plate. Then, the absorbance (OD 550-650 nm) was measured using an absorption spectrometer.

FIG. 10 shows the results. It is clarified that culture with the addition of AS, LS, RS, SS, PrS, FSK, or D4476 induced the ability to produce calcified matrix in fibroblasts.

Additionally, the culture with the addition of 10 nM PiS also achieved similar results to those of other statin compounds.

2-2: Alizarin Red S Staining (FIG. 11)

A normal human dermal fibroblast (HDF) strain was seeded in a 24-well plate at a concentration of $5\times10^3$ cells/well (day 0). On the next day, the culture medium was removed from each well, and replaced with fresh medium (500 µl/well). The induction medium was obtained by adding 10% FBS to Dulbecco's Modified Eagle's Medium (DMEM), 50 µg/ml ascorbic acid, 10 mM β-glycerophosphate, and 100 nM dexamethasone. Further, the small molecular compound as shown in the Figure was added. The culture medium was replaced once every 3 to 4 days, and culture was performed.

Twenty-eight days after the culture, the culture medium was aspirated from each well, and the cells were washed with PBS (−), followed by fixation with 10% formalin. After washing was performed 3 times with sterile distilled water, an Alizarin Red S staining solution was added, followed by incubation at room temperature for 15 minutes. The liquid was collected from each well, and transferred to a 96-well plate. Then, the absorbance (OD 550-650 nm) was measured using an absorption spectrometer. The wells after staining were washed with sterile distilled water, and then photographed.

Figure 11:
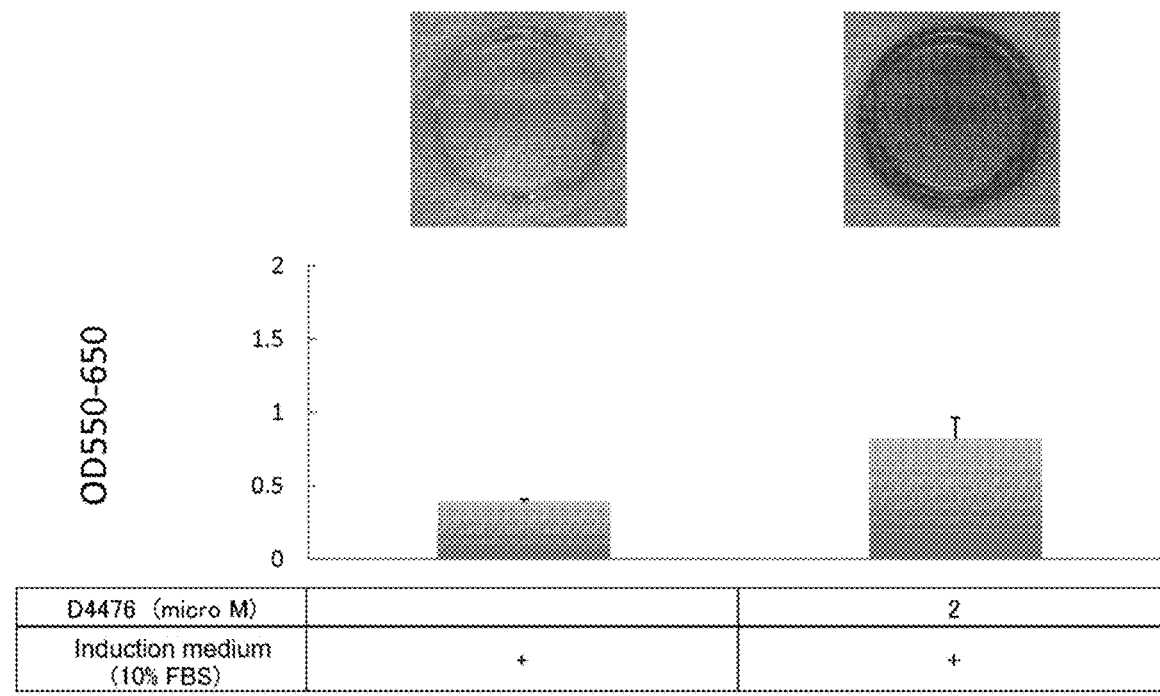
FIG. 11 shows Alizarin Red S staining images and intensity (28 days).

FIG. 11 shows the results. Calcified bone matrix is shown as red staining. It is clarified that culture with the addition of D4476 induced the ability to produce calcified matrix in fibroblasts.

2-3: Alizarin Red S Staining (FIG. 12)

A normal human dermal fibroblast (HDF) strain was seeded in a 24-well plate at a concentration of $5\times10^3$ cells/well (day 0). On the next day, the culture medium was removed from each well, and replaced with fresh medium (500 µl/well). The induction medium was obtained by adding 5% human serum to Dulbecco's Modified Eagle's Medium (DMEM), 50 µg/ml ascorbic acid, 10 mM β-glycerophosphate, and 100 nM dexamethasone. Further, the small molecular compound as shown in the Figure was added. The culture medium was replaced once every 3 to 4 days, and culture was performed.

Twenty-eight days after the culture, the culture medium was aspirated from each well, and the cells were washed with PBS (−), followed by fixation with 10% formalin. After washing was performed 3 times with sterile distilled water, an Alizarin Red S staining solution was added, followed by incubation at room temperature for 15 minutes. The liquid was collected from each well and transferred to a 96-well plate. Then, the absorbance (OD 550-650 nm) was measured using an absorption spectrometer. The wells after staining were washed with sterile distilled water, and then photographed.

Figure 12:
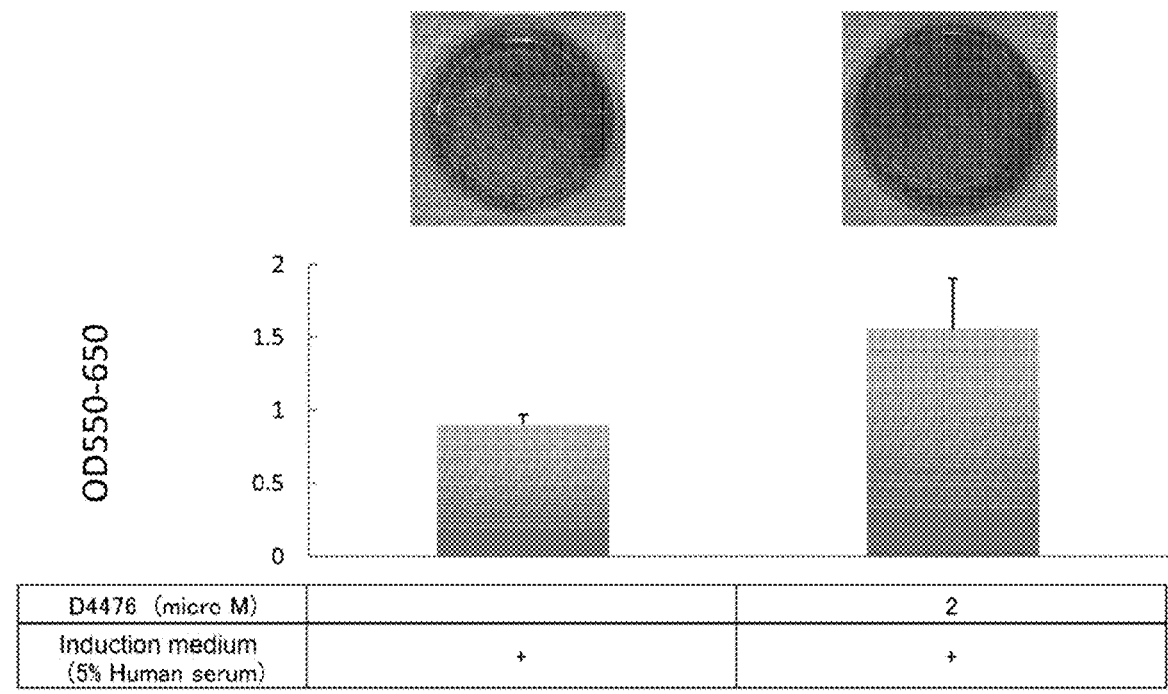
FIG. 12 shows Alizarin Red S staining images and intensity (28 days).

FIG. 12 shows the results. Calcified bone matrix is shown as red staining. It is clarified that culture with the addition of D4476 induced a higher ability to produce calcified matrix in fibroblasts.

2-4: Real-Time RT-PCR (FIG. 13)

The culture was performed as in "2-1" above by adding the stated compounds.

Twenty-eight days after the culture, the culture medium was removed from each well, and the cells were washed with PBS (−). Then, total RNA was collected from the cells using ISOGEN II, and cDNA was synthesized using ReverTra Ace qPCR RT Master Mix. Real-time PCR Master Mix, and a TaqMan probe and primers specific to a human alkaline phosphatase (ALP) gene were added, and real-time RT-PCR was performed using an AB7300 Real-Time PCR System. Furthermore, total RNA was extracted from osteoblasts from normal human bone, and analysis was performed in a similar manner.

Figure 13:
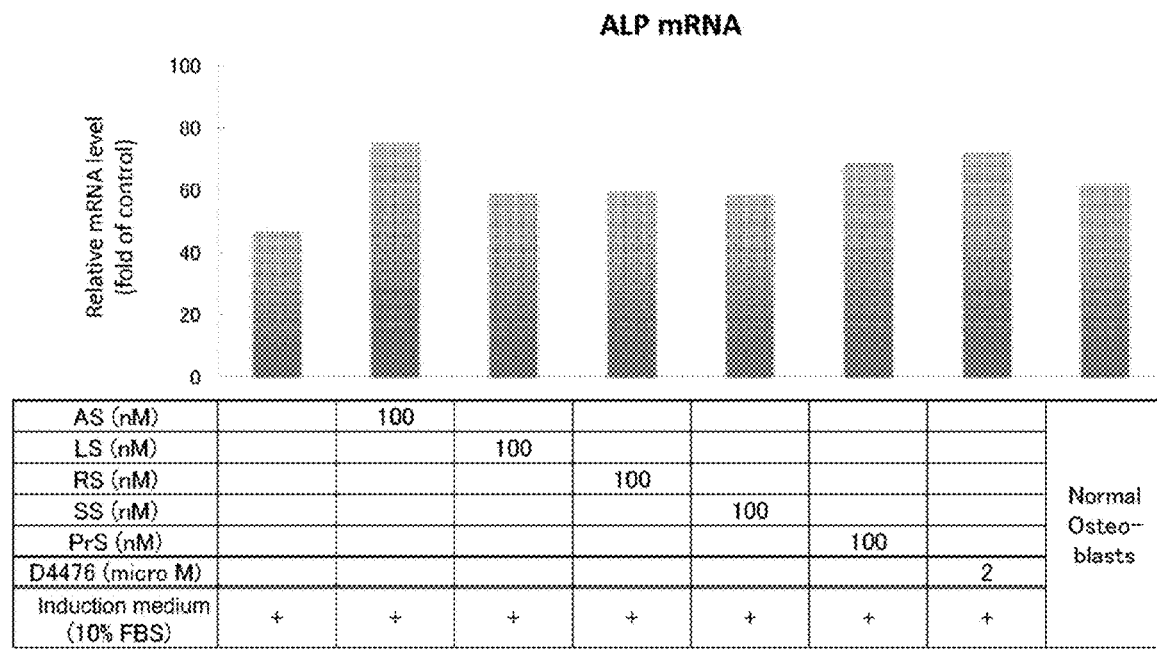
FIG. 13 shows ALP mRNA expression levels by real-time RT-PCR (28 days).

FIG. 13 shows the results with relative values that were calculated on the assumption that the value of normal human fibroblasts was 1. It is clarified that culture with the addition of AS, LS, RS, SS, PrS, or D4476 induced the mRNA expression of ALP gene.

2-5: Real-Time RT-PCR (FIG. 14)

The culture was performed as in "2-1" above by adding the stated compounds.

Twenty-eight days after the culture, the mRNA expression of ALP gene in the cells in each well was analyzed by real-time RT-PCR, as in Example 3. Furthermore, total RNA was extracted from osteoblasts from normal human bone, and analysis was performed in a similar manner.

Figure 14:
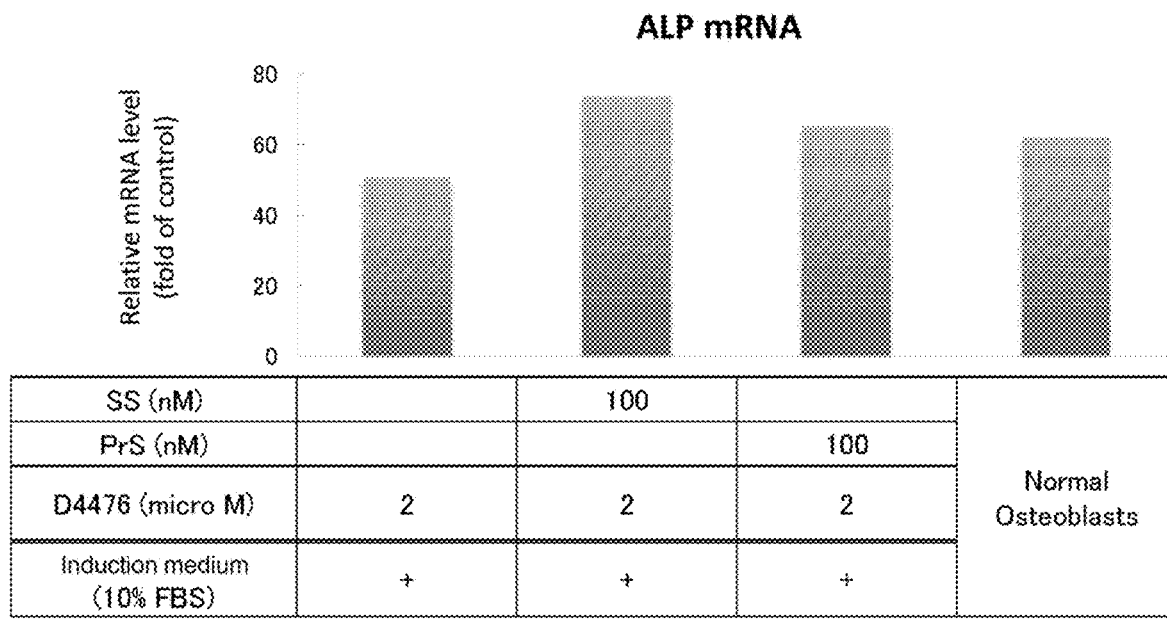
FIG. 14 shows ALP mRNA expression levels by real-time RT-PCR (28 days).

FIG. 14 shows the results with relative values that were calculated on the assumption that the value of normal human fibroblasts was 1. It is clarified that the addition of SS or PrS in combination with D4476 more strongly induced ALP expression, compared with when D4476 was added alone.

2-6: Real-Time RT-PCR (FIG. 15)

A normal human dermal fibroblast (HDF) strain was seeded in a 24-well plate at a concentration of $5 \times 10^3$ cells/well (day 0). On the next day, the culture medium was removed from each well, and replaced with fresh medium (500 μl/well). The induction medium was obtained by adding 5% human serum to Dulbecco's Modified Eagle's Medium (DMEM), 50 μg/ml ascorbic acid, 10 mM β-glycerophosphate, and 100 nM dexamethasone. Further, the small molecular compounds as shown in the Figure were added. The culture medium was replaced once every 3 to 4 days, and culture was performed.

Twenty-eight days after the culture, the mRNA expression of ALP gene in the cells in each well was analyzed by real-time RT-PCR, as in "2-3" above. Furthermore, total RNA was extracted from osteoblasts from normal human bone, and analysis was performed in a similar manner.

Figure 15:
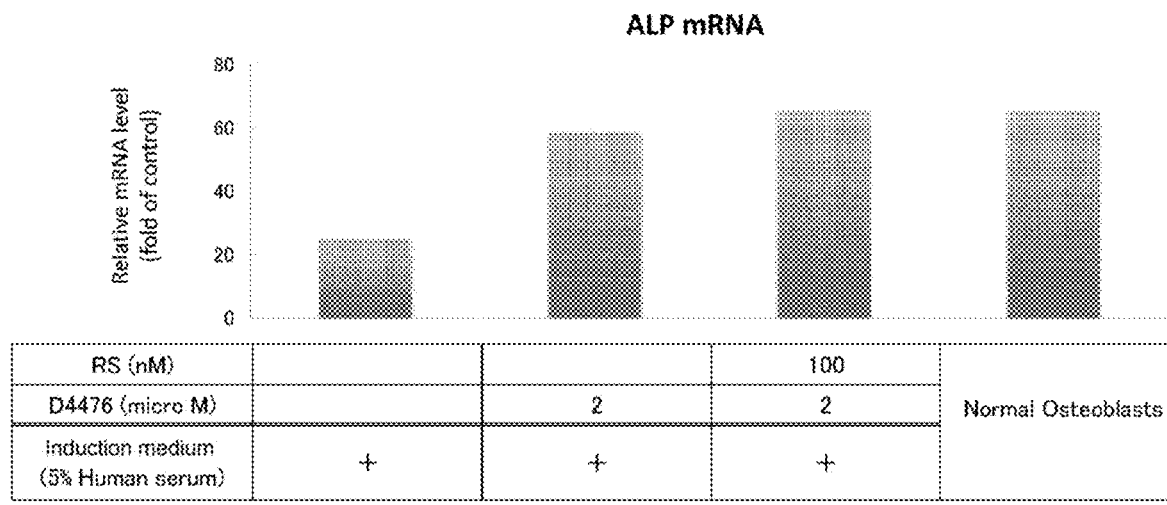
FIG. 15 shows ALP mRNA expression levels by real-time RT-PCR (28 days).

FIG. 15 shows the results with relative values that were calculated on the assumption that the value of normal human fibroblasts was 1. The addition of RS in combination with D4476 more strongly induced the ALP expression, compared with when D4476 was added alone.

2-7: Real-Time RT-PCR (FIG. 16)

The culture was performed as in "2-6" above by adding the stated compounds.

Twenty-eight days after the culture, the culture medium was removed from each well, and the cells were washed with PBS (−). Then, total RNA was collected from the cells using ISOGEN II, and cDNA was synthesized using Rever-Tra Ace qPCR RT Master Mix. Real-time PCR Master Mix, and a TaqMan probe and primers specific to human osteocalcin (OC) were added, and real-time RT-PCR was performed using an AB7300 Real-Time PCR System.

Figure 16:
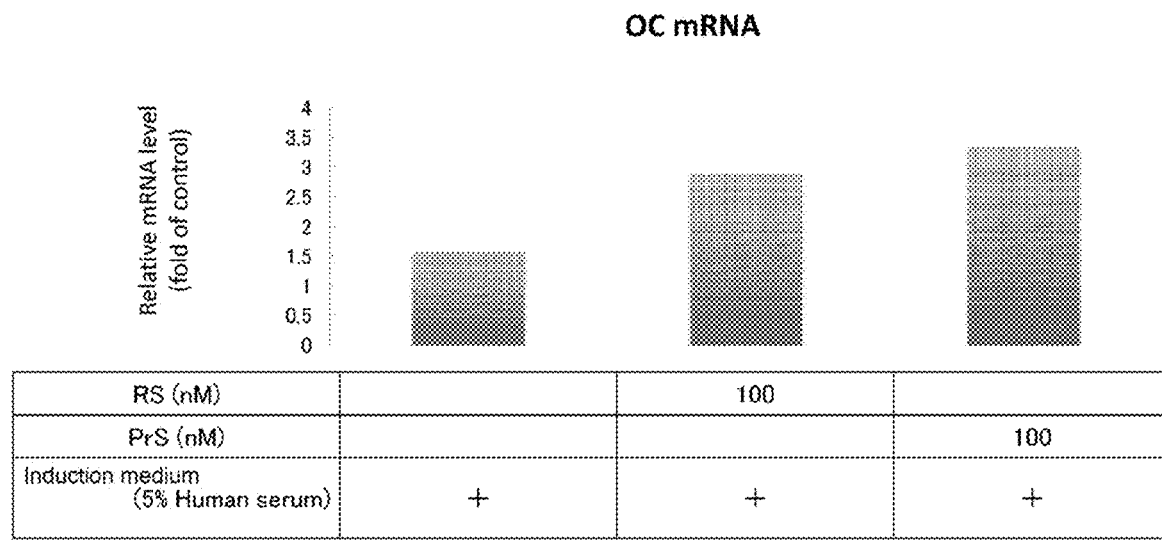
FIG. 16 shows osteocalcin (OC) mRNA expression levels by real-time RT-PCR (28 days).

FIG. 16 shows the results. It is clarified that culture with the addition of either RS or PrS induced the mRNA expression of osteocalcin.

2-8: Real-Time RT-PCR (FIG. 17)

The culture was performed as in "1" above by adding the stated compounds.

Twenty-eight days after the culture, the culture medium was removed from each well, and the cells were washed with PBS (−). Then, total RNA was collected from the cells using ISOGEN II, and cDNA was synthesized using Rever-Tra Ace qPCR RT Master Mix. Real-time PCR Master Mix, and a TaqMan probe and primers specific to human Runx2 gene were added, and real-time RT-PCR was performed using an AB7300 Real-Time PCR System.

Figure 17:
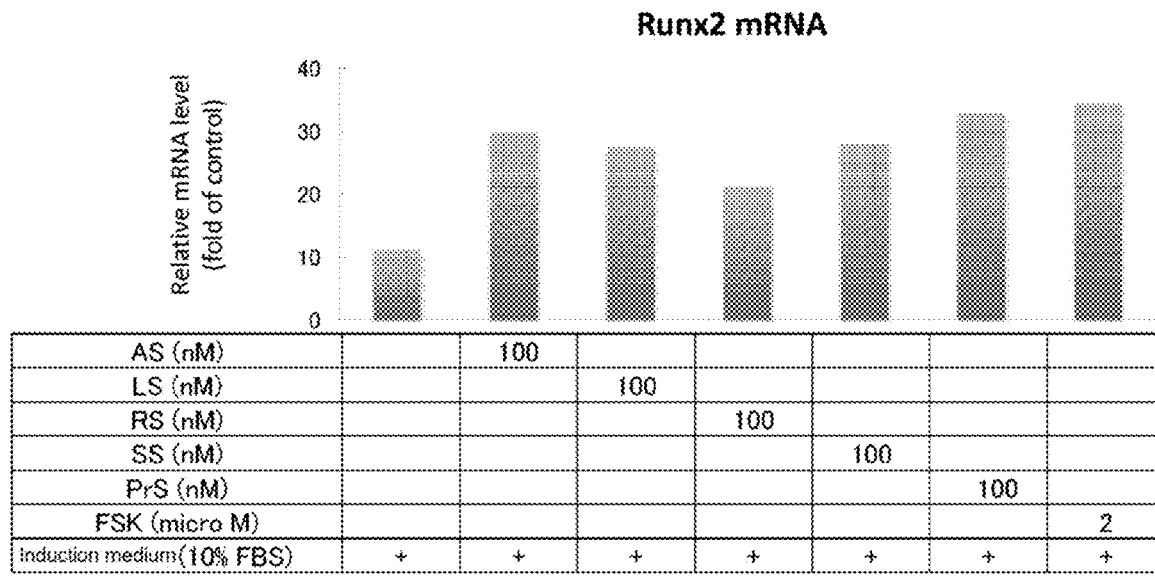
FIG. 17 shows Runx2 mRNA expression levels by real-time RT-PCR (28 days).

FIG. 17 shows the results. It is clarified that culture with the addition of AS, LS, RS, SS, PrS, or FSK induced the mRNA expression of Runx2 gene.

2-9: Real-Time RT-PCR (FIG. 18)

The culture was performed as in "2-1" above by adding the stated compounds.

Twenty-eight days after the culture, the culture medium was removed from each well, and the cells were washed with PBS (−). Then, total RNA was collected from the cells using ISOGEN II, and cDNA was synthesized using Rever-Tra Ace qPCR RT Master Mix. Real-time PCR Master Mix, and a TaqMan probe and primers specific to human osterix gene were added, and real-time RT-PCR was performed using an AB7300 Real-Time PCR System.

Figure 18:
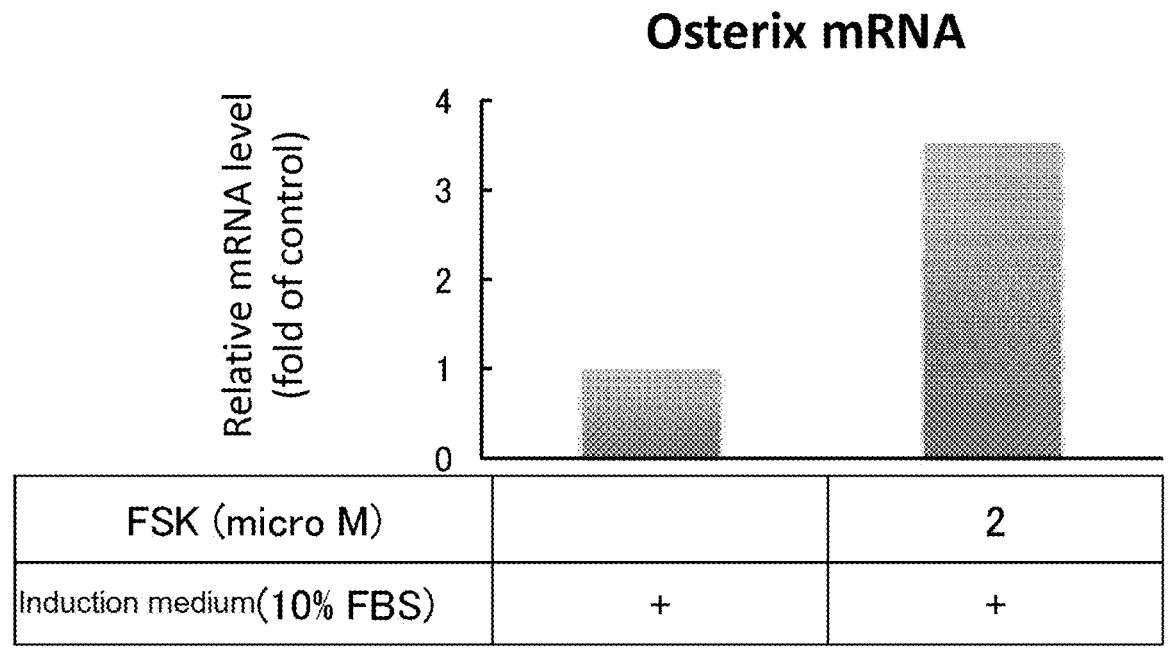
FIG. 18 shows osterix mRNA expression levels by real-time RT-PCR (28 days).

FIG. 18 shows the results. It is clarified that culture with the addition of FSK induced the mRNA expression of osterix gene.

2-10: Alizarin Red S Staining (FIG. 19)

The culture was performed as in Example 1 by adding the stated compounds. DZNep was purchased from Cayman Chemical (Ann Arbor, USA), and CX-4945 was purchased from Biovision (Zurich, Switzerland).

Twenty-eight days after the culture, as in Example 2, Alizarin Red S staining was performed, and the measurement of the absorbance (OD 550-650 nm) and photographing were performed.

Figure 19:
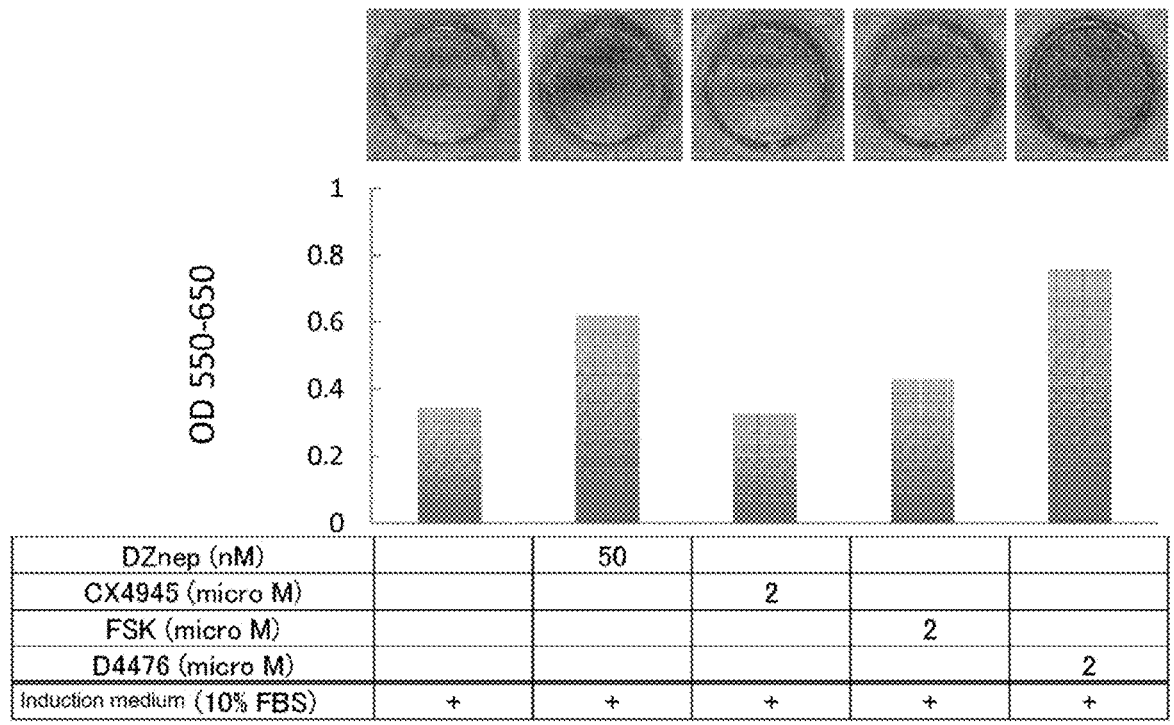
FIG. 19 shows Alizarin Red S staining images and intensity (28 days).

FIG. 19 shows the results. It is clarified that culture with the addition of D4476, FSK, or DZNep induced the ability to produce calcified matrix in fibroblasts. CX-4945 had no effect.

2-11: DNA Micro Array (FIG. 20)

A normal human dermal fibroblast (HDF) strain was seeded in a 60-mm culture dish, and cultured under standard conditions in an induction medium to which 100 nM simvastatin (SS), or 100 nM simvastatin and 2 μM D4476 (SS+D4) had been added. The medium was replaced once every 3 to 4 days, and culture was performed for 21 days. Then, total RNA was collected from the cells using ISOGEN II. Similarly, total RNA was collected from human dermal fibroblasts (HDFs) and human osteoblasts (OBs). The mRNA expression pattern of each cell was analyzed genome-wide using a DNA chip of Affymetrix, Inc.

Figure 20:
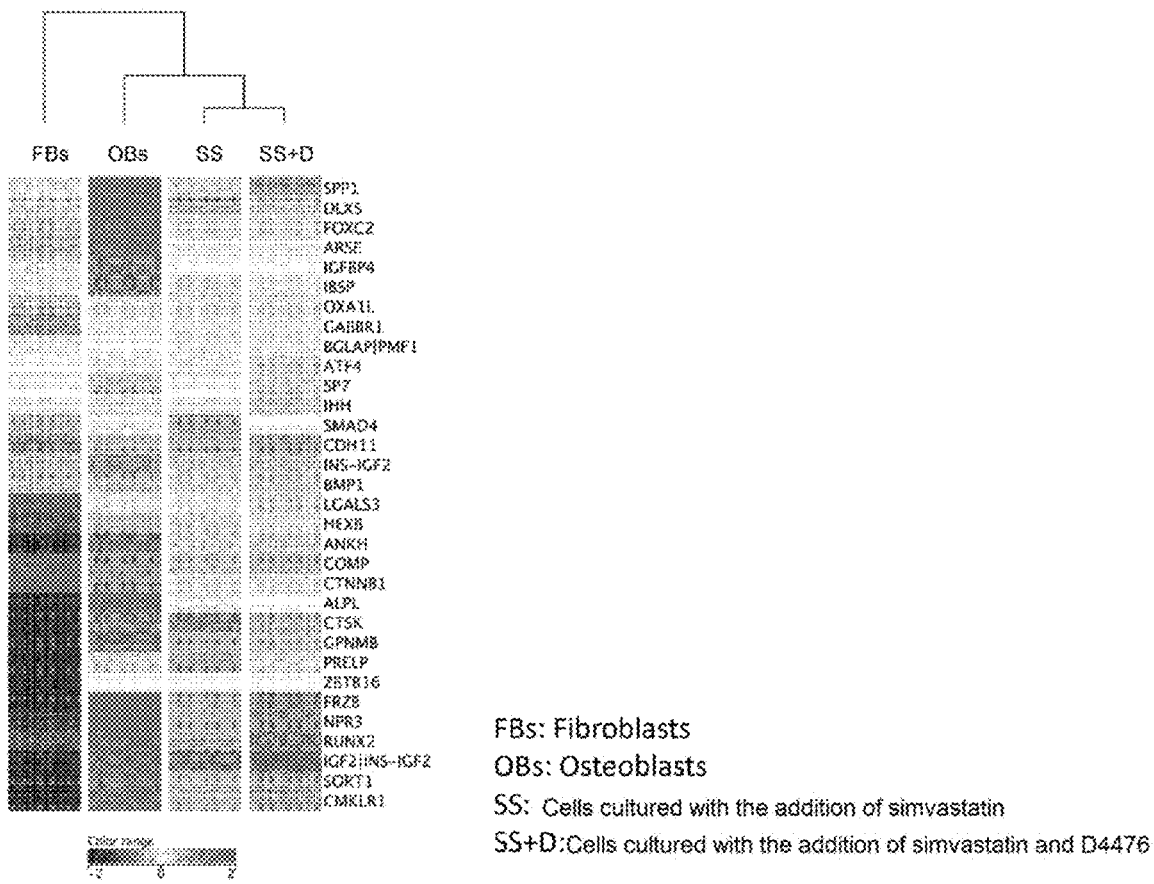
FIG. 20 shows the results of DNA microarray. In the figure, "FBs" represents fibroblasts, "OBs" represents osteoblasts, "SS" represents cells cultured with the addition of simvastatin, and "SS+D" represents cells cultured with the addition of simvastatin and D4476.

FIG. 20 shows the results. Both of the cells cultured with the addition of SS and cells cultured with the addition of SS+D4 showed global gene expression patterns similar to that of osteoblasts, rather than that of fibroblasts, and the latter showed a global gene expression pattern more similar to that of osteoblasts, compared with the former.

2-12: In Vivo Bone Formation (FIG. 21)

Animal experiments were carried out with the approval of Kyoto Prefectural University of Medicine. Eight-week-old male NOD/SCID mice (Charles River) were anesthetized by intraperitoneal injection with pentobarbital. A segmental bone defect having a diameter of about 4 mm was formed at the left femoral diaphysis using a dental drill while pouring water. Cells obtained by culturing HDFs in the presence of simvastatin and D4476 for 21 days as in Example 11 were suspended in a 1:1 liquid mixture of 50 μL of medium and 50 μL of Matrigel (BD Biosciences, San Jose, Calif.), and transplanted to the bone defect site and the bone surface around the defect site at a concentration of $5 \times 10^3$ cells/mouse. Mice in which a bone defect was formed and fibroblasts were then transplanted were also prepared. Twenty-one days later, the mice were euthanized, the thigh was excised and fixed with neutral formalin, and then microcomputed tomography (μCT) was conducted using an X-ray CT device (Scan Xmate-L090, Com Scan Techno, Yokohama, Japan).

Figure 21:
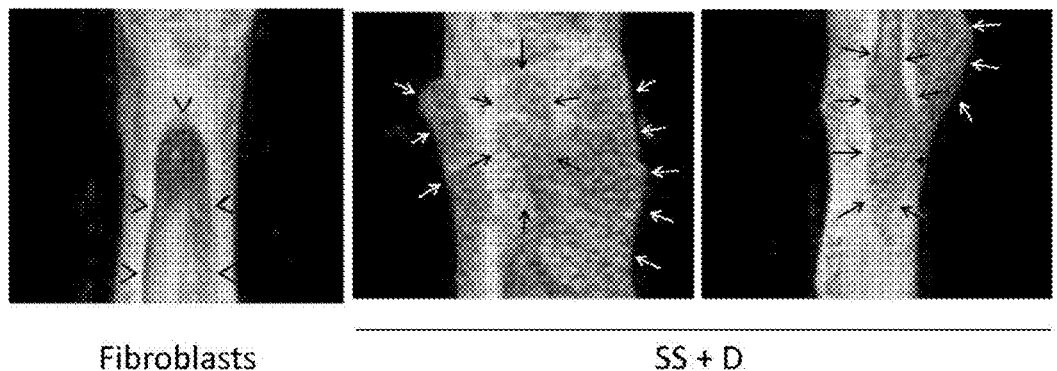
FIG. 21 shows in vivo bone formation (μCT images).
(Left figure: fibroblasts) the femur in which an artificial bone defect was formed, and fibroblasts were then transplanted. The arrowheads show the bone defect remaining at the site in which the artificial bone defect was formed, and transplantation was performed.
(Right figures: SS+D) the femur in which an artificial bone defect was formed and cells cultured with the addition of simvastatin and D4476 were transplanted. The black arrows show that bone has been regenerated to repair the defect at the site in which the artificial bone defect was formed and transplantation was performed. The white arrows show that bone has been regenerated at the site around the defect, at which transplantation was performed. The arrowheads show the bone defect remaining at the site in which the artificial bone defect was formed and transplantation was performed.

FIG. 21 shows three-dimensionally constructed μCT images. The black arrows show that bone has been regenerated to repair a defect at the site in which an artificial bone defect was formed and transplantation was performed. The white arrows show that bone has been regenerated at the site around the defect, at which transplantation was performed. The arrowheads show the bone defect remaining at the site in which the artificial bone defect was formed and transplantation was performed. It was clarified that the cells cultured with the addition of simvastatin (SS) plus D4476 (D) have the ability of bone formation in vivo.

2-13: In Vivo Bone Formation (FIG. 22)

Animal experiments were carried out with the approval of the Kyoto Prefectural University of Medicine. A transplantation experiment was performed as in "2-12" above, and mice to which fibroblasts were transplanted were also prepared. Twenty-one days later, the mice were euthanized, and the thigh was excised and fixed with neutral formalin as in Example 11. Then, the bone tissue was embedded in SCEM compound (Leica Microsystems) and frozen rapidly. The tissue was sliced into 6-μm sections, and then the serial sections were stained with hematoxylin eosin (H&E) (left) and Alizarin Red S (right).

Figure 22:
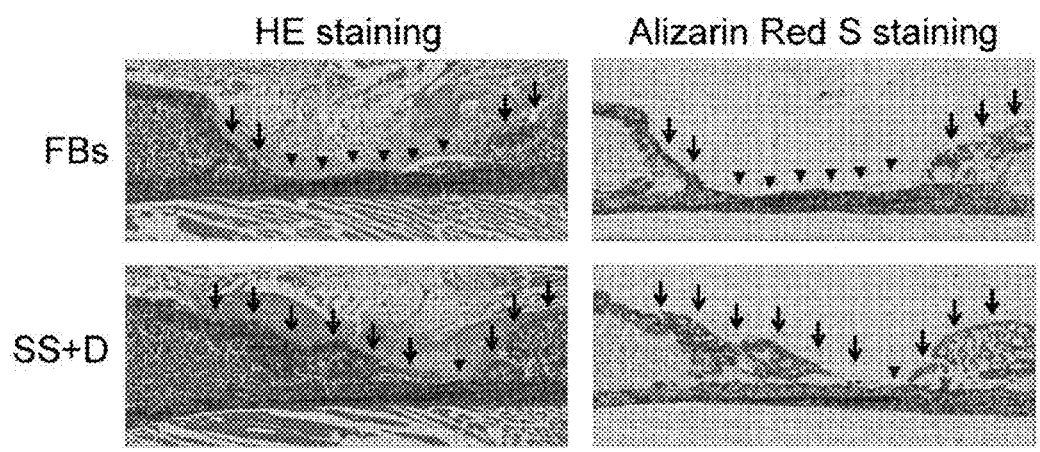
FIG. 22 shows in vivo bone formation (HE staining and Alizarin Red S staining). "FBs" is the femur in which an artificial bone defect was formed and fibroblasts were transplanted. "SS+D" is the femur in which an artificial bone defect was formed, and cells cultured with the addition of simvastatin and D4476 were transplanted. The triangles indicate the site in which an artificial bone defect was formed and transplantation was performed, and in which the bone defect remains. The arrows show the site in which the artificial bone defect was formed and transplantation was performed, and in which bone has been regenerated to repair the defect.

FIG. 22 shows the results. It was clarified that the cells cultured with the addition of SS+D4476 have the ability of bone formation in vivo.

Figure 23:
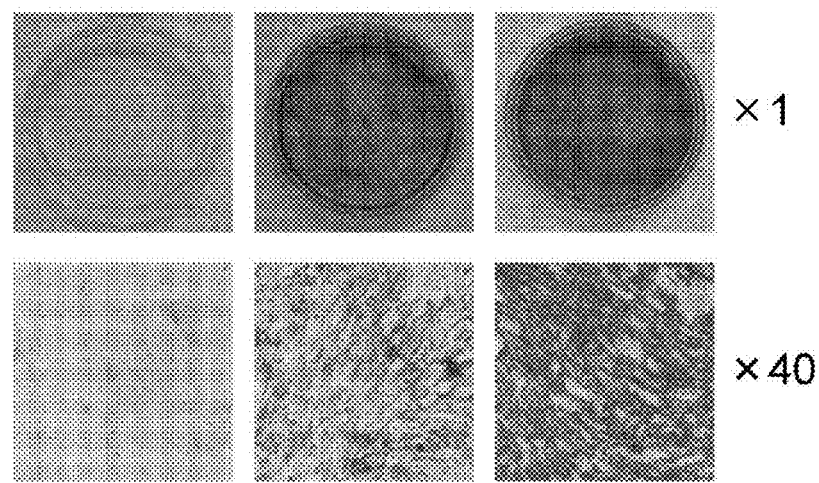
FIG. 23 shows Alizarin Red S staining images (normal human white preadipocytes, 21 days).

2-14: Induction from Normal Human White Preadipocytes (FIG. 23)

Normal human white preadipocytes (HWPs) were seeded in a 35-mm dish at a concentration of $5 \times 10^4$ cells/dish (day 0). On the next day, the culture medium was removed from each well and replaced with fresh medium (2 mL/well) (a general-purpose medium or an induction medium that contains the small molecular compound as shown in the Figure).

The general-purpose medium was obtained by adding 10% FBS to Dulbecco's Modified Eagle's Medium (DMEM), and the induction medium was obtained by adding 50 μg/mL ascorbic acid, 10 mM β-glycerophosphate, 100 nM dexamethasone, and 10% FBS to DMEM. The culture medium was replaced once every 3 to 4 days, and culture was performed.

Twenty-one days after the culture, the culture medium was aspirated from each well, and the cells were washed with PBS (−), followed by fixation with 10% formalin. After washing was performed 3 times with sterile distilled water, an Alizarin Red S staining solution was added, followed by incubation at room temperature for 15 minutes. The wells after staining were washed with sterile distilled water, and then photographed.

FIG. 23 shows the results. Calcified bone matrix is shown as red staining. It is clarified that the culture with the addition of D4476 strongly induced the ability to produce calcified matrix in HWPs.

The invention claimed is:

1. A method for preparing osteoblasts, the method comprising culturing mammal differentiated somatic cells in a medium in the presence of at least one statin compound to convert the somatic cells into osteoblasts, and
wherein the somatic cells are fibroblasts, gingival cells, or adipocytes.

2. The method according to claim 1, wherein the medium is an osteoblast induction medium.

3. The method according to claim 2, wherein the osteoblast induction medium comprises ascorbic acid, β-glycerophosphate and glucocorticoid.

* * * * *